US008012685B2

(12) United States Patent
Shannon et al.

(10) Patent No.: US 8,012,685 B2
(45) Date of Patent: Sep. 6, 2011

(54) DETECTION OF ANALYTES AND NUCLEIC ACIDS

(75) Inventors: Mark E. Shannon, San Francisco, CA (US); David W. Ruff, San Francisco, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 129 days.

(21) Appl. No.: 11/888,656

(22) Filed: Jul. 31, 2007

(65) Prior Publication Data

US 2008/0032310 A1 Feb. 7, 2008

Related U.S. Application Data

(60) Provisional application No. 60/835,118, filed on Aug. 1, 2006.

(51) Int. Cl.
*C12Q 1/68* (2006.01)
*G01N 33/53* (2006.01)
*C07H 21/02* (2006.01)
*C07H 21/04* (2006.01)

(52) U.S. Cl. ............. 435/6; 435/7.1; 536/23.1; 536/24.3

(58) Field of Classification Search ..... 435/6; 536/22.1, 536/23.1, 24.3
See application file for complete search history.

(56) References Cited

U.S. PATENT DOCUMENTS

| | | | | |
|---|---|---|---|---|
| 4,988,617 A * | 1/1991 | Landegren et al. | ............... | 435/6 |
| 5,534,410 A * | 7/1996 | Tjian et al. | ......... | 435/6 |
| 5,665,539 A * | 9/1997 | Sano et al. | .......... | 435/6 |
| 5,863,726 A * | 1/1999 | Harley et al. | ...... | 435/6 |
| 5,874,260 A | 2/1999 | Cleuziat et al. | | |
| 5,876,924 A * | 3/1999 | Zhang et al. | ....... | 435/5 |
| 5,935,825 A * | 8/1999 | Nishimura et al. | .......... | 435/91.2 |
| 6,210,915 B1 * | 4/2001 | Shay et al. | ......... | 435/15 |
| 6,333,157 B1 * | 12/2001 | Miller-Jones et al. | ............ | 435/6 |
| 6,511,809 B2 | 1/2003 | Baez et al. | | |
| 6,762,027 B2 * | 7/2004 | Greenfield et al. | ............... | 435/6 |
| 2002/0064779 A1 | 5/2002 | Landegren et al. | | |
| 2002/0102591 A1 | 8/2002 | Sorge | | |
| 2003/0148525 A1 | 8/2003 | Wang | | |
| 2004/0248103 A1 | 12/2004 | Feaver et al. | | |
| 2005/0003361 A1 | 1/2005 | Fredriksson | | |
| 2005/0181508 A1 | 8/2005 | Fredriksson et al. | | |
| 2005/0282158 A1 | 12/2005 | Landegren | | |
| 2006/0214104 A1 * | 9/2006 | Pope et al. | .................... | 250/297 |
| 2006/0223071 A1 * | 10/2006 | Wisniewski et al. | .............. | 435/6 |
| 2006/0241072 A1 * | 10/2006 | Baker | ............................ | 514/44 |
| 2007/0026430 A1 | 2/2007 | Andersen et al. | | |
| 2007/0134648 A1 * | 6/2007 | Soskic | ............... | 435/4 |
| 2008/0050731 A1 * | 2/2008 | Agnew et al. | .................... | 435/6 |
| 2008/0064071 A1 * | 3/2008 | Hogrefe et al. | ............. | 435/91.2 |
| 2008/0187924 A1 * | 8/2008 | Korfhage et al. | ................. | 435/6 |
| 2008/0220979 A1 * | 9/2008 | Wang et al. | ....................... | 506/9 |

FOREIGN PATENT DOCUMENTS

| | | | |
|---|---|---|---|
| EP | 1 566 437 A1 | | 8/2005 |
| WO | WO 99/32654 | * | 7/1999 |
| WO | WO 00/56920 | * | 2/2000 |
| WO | WO 01/61037 A1 | | 8/2001 |
| WO | WO 03/044231 A1 | | 5/2003 |
| WO | WO 03/64605 | * | 8/2003 |
| WO | WO 03/104385 A1 | | 12/2003 |
| WO | WO 2004/027082 A2 | | 4/2004 |
| WO | WO 2005/040194 A2 | | 5/2005 |
| WO | WO 2005/123963 A2 | | 12/2005 |

OTHER PUBLICATIONS

Sims et al., Immunopolymaerase Chain Reaction using Real-time Polymerase Chain Reaction. Analytical Biochemistry 281 : 230-232 (2000).*
Sano et al., Immuno-PCR : Very sensitive antigen detection by means of specific antibody-DNA conjugates. Science 258: 120-122 (1992).*
Pai et al. Proximity ligation assays with peptide conjugate 'burrs' for the sensitive detection of spores. Nucleic Acids Research 33(18) : e162 (2005).*
Eis et al., An invasive cleavage assay for direct quantification of specific RNAs. Nature Biotechnology 19 :673-676 (Jul. 2001).*
Neophytou et al., Development of a procedure for the direct cloning of T-cell epitopes using bacterial expression systems. Journal of immunological Methods 196 : 63-72 (1996).*
Vuillard et al., Non-detergent sulphobetaines: a new class of mild solubilization agents for protein purification. Biochemical Journal 305 : 337-343 (1995).*
Di Giusto et al., "Construction, Stability, and Activity of Multivalent Circular Anticoagulant Aptamers," *J. Biol. Chem.*, 279(45):46483-46489 (2004).
Di Giusto et al., "Proximity extension of circular DNA aptamers with real-time protein detection," *Nucl. Acids Res.*, 33(6):e64 (published online 2005).
Gustafsdottir et al., "Detection of Individual Microbial Pathogens by Proximity Ligation," *Clin. Chem.*, 52(6):1152-1160 (2006).
Fredriksson et al., "Protein detection using proximity-dependent DNA ligation assays," *Nature Biotech.*, 20:473-477 (2002).
Office Action mailed Apr. 12, 2007, in U.S. Appl. No. 11/428,191.
Amendment and Response filed Aug. 13, 2007 in U.S. Appl. No. 11/428,191.
Office Action mailed Oct. 22, 2007, in U.S. Appl. No. 11/428,191.
International Search Report and Written Opinion dated Dec. 20, 2007, in PCT Application No. PCT/US2007/017187.
Gustafsdottir et al., "Proximity ligation assays for sensitive and specific protein analyses," Anal. Biochem. 345(1): 2-9 (2005).
Gullberg et al., "Cytokine detection by antibody-based proximity ligation," Proc. Nat. Acad. Sci. U.S.A. 101(22): 8420-8424 (2004).
Gullberg et al., "A sense of closeness: protein detection by proximity ligation," Current Opin. Biotechnol. 14(1): 82-86 (2003).
Cao, "Recent developments in ligase-mediated amplification and detection," Trends Biotechnol. 22(1): 38-44 (2004).
EP 07810985.7 EP Examination Report, mailed Jan. 5, 2010.
PCT/US2007/017187 "Written Opinion of the International Searching Authority," issued Feb. 3, 2009.
PCT/US2007/017187 "International Preliminary Report on Patentability," issued Feb. 3, 2009.

* cited by examiner

*Primary Examiner* — Ethan C Whisenant

(57) ABSTRACT

Methods of detecting at least one analyte and at least one nucleic acid in a sample are provided. Reagents for carrying out the methods are also provided.

17 Claims, 22 Drawing Sheets

DETECTION OF ANALYTES AND NUCLEIC ACIDS

This application claims the benefit of U.S. Provisional Application No. 60/835,118, filed Aug. 1, 2006. U.S. Provisional Application No. 60/835,118 is incorporated by reference herein in its entirety for any purpose.

FIELD

Methods of detecting at least one analyte and at least one nucleic acid in a sample are provided. Reagents for carrying out the methods are also provided.

BACKGROUND

Various methods of detecting proteins in cell lysates, including Western blotting, ELISA, etc., are known in the art. Various methods of detecting nucleic acids in cell lysates, including RT-PCR, etc., are also known in the art. The relative amounts of detected proteins and detected nucleic acids in a sample can be difficult to compare, however, because the samples are generally prepared separately and by different methods. Furthermore, different detection methods used for proteins and nucleic acids may also lead to difficulty in correlating their relative amounts.

SUMMARY

In various embodiments, a method of detecting at least one target analyte and at least one target nucleic acid in a cell is provided. In various embodiments, a method comprising lysing a cell in a multifunctional lysis buffer to produce a cell lysate, detecting at least one target analyte in the cell lysate using a proximity detection assay, and detecting at least one target nucleic acid in the cell lysate using a quantitative nucleic acid detection assay, is provided. In various embodiments, detecting at least one target analyte and detecting at least one target nucleic acid occur in the same vessel.

In various embodiments, a method comprising lysing a cell in a multifunctional lysis buffer to produce a cell lysate, incubating the cell lysate with (i) at least one proximity detection probe set, wherein each proximity detection probe set comprises at least two proximity detection probes, and wherein each proximity detection probe comprises at least one analyte binding moiety and at least one oligonucleotide moiety; (ii) at least one splint oligonucleotide; and (iii) at least one ligase, such that at least one ligated proximity detection probe set is formed; incubating the cell lysate with at least one protease; detecting the at least one ligated proximity detection probe set; and detecting at least one target nucleic acid is provided.

In various embodiments, a method comprising lysing a cell in a multifunctional lysis buffer to produce a cell lysate, incubating the cell lysate with at least one proximity detection probe set, wherein each proximity detection probe set comprises at least two proximity detection probes, and wherein each proximity detection probe comprises at least one analyte binding moiety and at least one oligonucleotide moiety, such that at least one hybridized proximity detection probe set is formed; incubating the cell lysate with at least one protease; detecting the at least one hybridized proximity detection probe set; and detecting at least one target nucleic acid is provided.

In various embodiments, a multifunctional lysis buffer is provided. In various embodiments, a multifunctional lysis buffer comprises at least one chemical selected from NDSB-201, LDAO, CHAPS, DEDTAB, Zwittergent 3-10, and CAPSO.

In various embodiments, a kit for detecting at least one target analyte and at least one target nucleic is acid provided. In various embodiments, a kit comprises at least one multifunctional lysis buffer comprising at least one chemical selected from NDSB-201, LDAO, CHAPS, DEDTAB, Zwittergent 3-10, and CAPSO.

In various embodiments, a composition comprising a lysate, wherein the lysate comprises a multifunctional lysis buffer comprising at least one chemical selected from NDSB-201, LDAO, CHAPS, DEDTAB, Zwittergent 3-10, and CAPSO, and at least one proximity detection probe set, is provided.

DETAILED DESCRIPTION OF CERTAIN EMBODIMENTS

Figure 1:
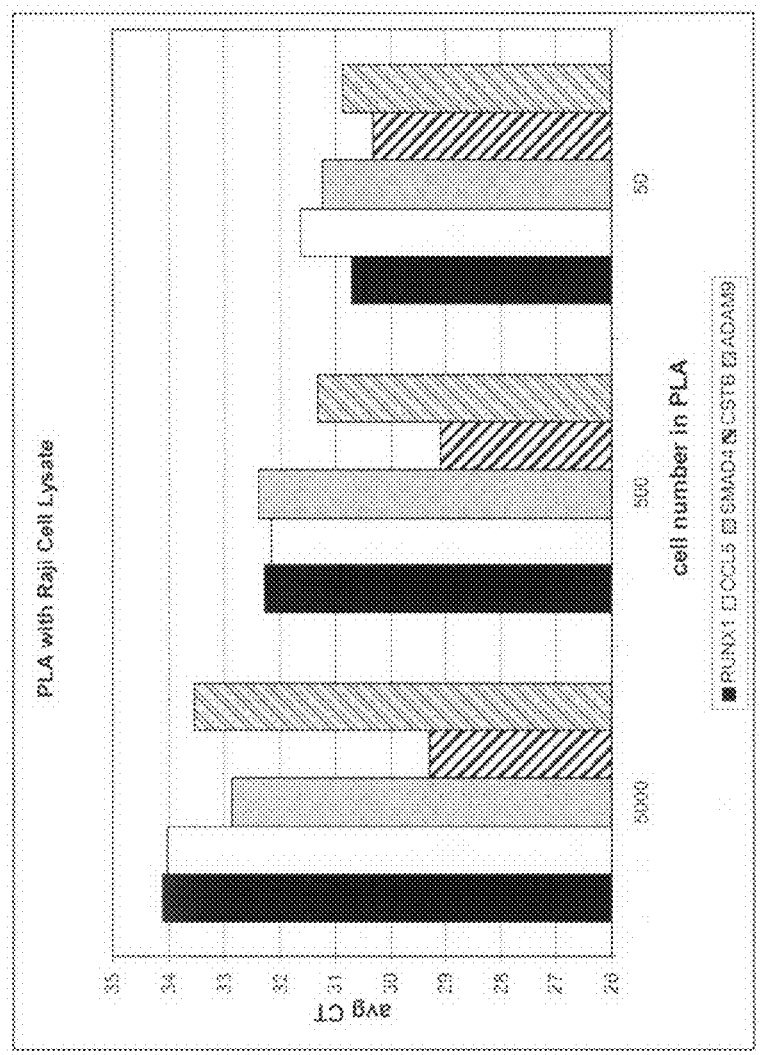
FIG. 1 shows the results of the proximity ligation assay described in Example 1. The threshold cycle number ("avg CT") for each reaction is shown.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents defines a term that contradicts that term's definition in this application, this application controls.

The use of the singular includes the plural unless specifically stated otherwise. The word "a" or "an" means "at least one" unless specifically stated otherwise. The use of "or" means "and/or" unless stated otherwise. The use of "or" in the context of multiply dependent claims means the alternative only. The meaning of the phrase "at least one" is equivalent to the meaning of the phrase "one or more." Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

In this specification, discussion of detecting "a" moiety, such as a target analyte, encompasses one or more of that moiety unless specifically stated otherwise.

All ranges discussed herein include the endpoints and all values between the endpoints Definitions The term "nucleotide base" refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases, e.g., adenine, guanine, cytosine, uracil, and thymine, and analogs of the naturally occurring nucleotide bases, e.g., 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2ms6iA), N2-dimethylguanine (dmG), 7-methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide" refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Exemplary riboses include, but are not limited to, 2'-(C1-C6) alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352, and WO 99/14226). Exemplary LNA sugar analogs within a polynucleotide include, but are not limited to, the structures:

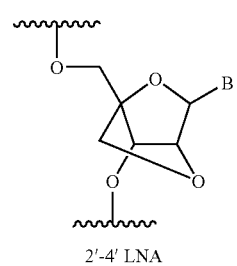

2'-4' LNA

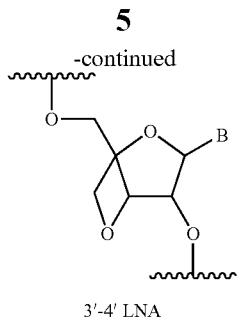

3'-4' LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the $N^9$-position of the nucleotide base. When the nucleotide base is pyrimidine, e.g. C, T or U, the pentose sugar is attached to the $N^1$-position of the nucleotide base, except for pseudouridines, in which the pentose sugar is attached to the C5 position of the uracil nucleotide base (see, e.g., Kornberg and Baker, (1992) *DNA Replication*, $2^{nd}$ Ed., Freeman, San Francisco, Calif.).

One or more of the pentose carbons of a nucleotide may be substituted with a phosphate ester having the formula:

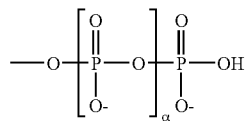

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleotide chemistry, see, e.g., Shabarova, Z. and Bogdanov, A. *Advanced Organic Chemistry of Nucleic Acids*, VCH, New York, 1994.

The term "nucleotide analog" refers to embodiments in which the pentose sugar and/or the nucleotide base and/or one or more of the phosphate esters of a nucleotide may be replaced with its respective analog. In certain embodiments, exemplary pentose sugar analogs are those described above. In certain embodiments, the nucleotide analogs have a nucleotide base analog as described above. In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers which can be polymerized into polynucleotide analogs in which the DNA/RNA phosphate ester and/or sugar phosphate ester backbone is replaced with a different type of internucleotide linkage. Exemplary polynucleotide analogs include, but are not limited to, peptide nucleic acids, in which the sugar phosphate backbone of the polynucleotide is replaced by a peptide backbone.

As used herein, the terms "polynucleotide", "oligonucleotide", and "nucleic acid" are used interchangeably and refer to single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$ and the like. A polynucleotide may be composed entirely of deoxyribonucleotides, entirely of ribonucleotides, or chimeric mixtures thereof. The nucleotide monomer units may comprise any of the nucleotides described herein, including, but not limited to, nucleotides and nucleotide analogs. A polynucleotide may comprise one or more lesions. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine or an analog thereof, "C" denotes deoxycytidine or an analog thereof, "G" denotes deoxyguanosine or an analog thereof, and "T" denotes thymidine or an analog thereof, unless otherwise noted.

Polynucleotides may be composed of a single type of sugar moiety, e.g., as in the case of RNA and DNA, or mixtures of different sugar moieties, e.g., as in the case of RNA/DNA chimeras. In certain embodiments, nucleic acids are ribopolynucleotides and 2'-deoxyribopolynucleotides according to the structural formulae below:

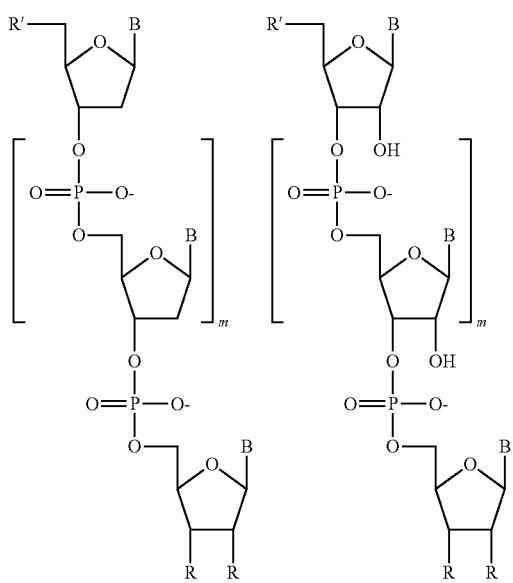

wherein each B is independently the base moiety of a nucleotide, e.g., a purine, a 7-deazapurine, a pyrimidine, or an analog thereof; each m defines the length of the respective nucleic acid and can range from zero to thousands, tens of thousands, or even more; each R is independently selected from the group comprising hydrogen, hydroxyl, halogen, —R", —OR", and —NR"R", where each R" is independently $(C_1-C_6)$ alkyl or $(C_5-C14)$ aryl, or two adjacent Rs may be taken together to form a bond such that the ribose sugar is 2',3'-didehydroribose, and each R' may be independently hydroxyl or

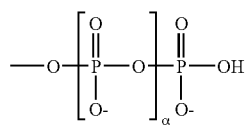

where α is zero, one or two.

In certain embodiments of the ribopolynucleotides and 2'-deoxyribopolynucleotides illustrated above, the nucleotide bases B are covalently attached to the C1' carbon of the sugar moiety as previously described.

The terms "nucleic acid", "polynucleotide", and "oligonucleotide" may also include nucleic acid analogs, polynucleotide analogs, and oligonucleotide analogs. The terms "nucleic acid analog", "polynucleotide analog" and "oligonucleotide analog" are used interchangeably, and refer to a polynucleotide that contains at least one nucleotide analog and/or at least one phosphate ester analog and/or at least one pentose sugar analog. A polynucleotide analog may comprise one or more lesions. Also included within the definition of polynucleotide analogs are polynucleotides in which the phosphate ester and/or sugar phosphate ester linkages are replaced with other types of linkages, such as N-(2-aminoethyl)-glycine amides and other amides (see, e.g., Nielsen et al., 1991, *Science* 254: 1497-1500; WO 92/20702; U.S. Pat. Nos. 5,719,262; 5,698,685); morpholinos (see, e.g., U.S. Pat. Nos. 5,698,685; 5,378,841; 5,185,144); carbamates (see, e.g., Stirchak & Summerton, 1987, *J. Org. Chem.* 52: 4202); methylene(methylimino) (see, e.g., Vasseur et al., 1992, *J. Am. Chem. Soc.* 114: 4006); 3'-thioformacetals (see, e.g., Jones et al., 1993, *J. Org. Chem.* 58: 2983); sulfamates (see, e.g., U.S. Pat. No. 5,470,967); 2-aminoethylglycine, commonly referred to as PNA (see, e.g., Buchardt, WO 92/20702; Nielsen (1991) Science 254:1497-1500); and others (see, e.g., U.S. Pat. No. 5,817,781; Frier & Altman, 1997, *Nucl. Acids Res.* 25:4429 and the references cited therein). Phosphate ester analogs include, but are not limited to, (i) $C_1$-$C_4$ alkylphosphonate, e.g. methylphosphonate; (ii) phosphoramidate; (iii) $C_1$-$C_6$ alkyl-phosphotriester; (iv) phosphorothioate; and (v) phosphorodithioate.

The terms "annealing" and "hybridization" are used interchangeably and refer to the base-pairing interaction of one nucleic acid with another nucleic acid that results in formation of a duplex, triplex, or other higher-ordered structure. In certain embodiments, the primary interaction is base specific, e.g., A/T and G/C, by Watson/Crick and Hoogsteen-type hydrogen bonding. Base-stacking and hydrophobic interactions may also contribute to duplex stability.

In this application, a statement that one sequence is the same as or is complementary to another sequence encompasses situations where both of the sequences are completely the same as or complementary to one another, and situations where only a portion of one of the sequences is the same as, or is complementary to, a portion or the entire other sequence. Here, the term "sequence" encompasses, but is not limited to, nucleic acid sequences, polynucleotides, oligonucleotides, probes, primers, primer-specific portions, and target-specific portions.

In this application, a statement that one sequence is complementary to another sequence encompasses situations in which the two sequences have mismatches. Despite the mismatches, the two sequences should selectively hybridize to one another under appropriate conditions.

The term "selectively hybridize" means that, for particular identical sequences, a substantial portion of the particular identical sequences hybridize to a given desired sequence or sequences, and a substantial portion of the particular identical sequences do not hybridize to other undesired sequences. A "substantial portion of the particular identical sequences" in each instance refers to a portion of the total number of the particular identical sequences, and it does not refer to a portion of an individual particular identical sequence. In certain embodiments, "a substantial portion of the particular identical sequences" means at least 70% of the particular identical sequences. In certain embodiments, "a substantial portion of the particular identical sequences" means at least 80% of the particular identical sequences. In certain embodiments, "a substantial portion of the particular identical sequences" means at least 90% of the particular identical sequences. In certain embodiments, "a substantial portion of the particular identical sequences" means at least 95% of the particular identical sequences.

In certain embodiments, the number of mismatches that may be present may vary in view of the complexity of the composition. Thus, in certain embodiments, the more complex the composition, the more likely undesired sequences will hybridize. For example, in certain embodiments, with a given number of mismatches, a probe may more likely hybridize to undesired sequences in a composition with the entire genomic DNA than in a composition with fewer DNA sequences, when the same hybridization and wash conditions are employed for both compositions. Thus, that given number of mismatches may be appropriate for the composition with fewer DNA sequences, but fewer mismatches may be more optimal for the composition with the entire genomic DNA.

In certain embodiments, sequences are complementary if they have no more than 20% mismatched nucleotides. In certain embodiments, sequences are complementary if they have no more than 15% mismatched nucleotides. In certain embodiments, sequences are complementary if they have no more than 10% mismatched nucleotides. In certain embodiments, sequences are complementary if they have no more than 5% mismatched nucleotides. In various embodiments, sequences are complementary if they have 0%, 1%, 2%, or 3% mismatched nucleotides.

In this application, a statement that one sequence hybridizes or binds to another sequence encompasses situations where the entirety of both of the sequences hybridize or bind to one another, and situations where only a portion of one or both of the sequences hybridizes or binds to the entire other sequence or to a portion of the other sequence. Here, the term "sequence" encompasses, but is not limited to, nucleic acid sequences, polynucleotides, oligonucleotides, probes, primers, primer-specific portions, and target-specific portions.

The term "primer" or "oligonucleotide primer" as used herein, refers to an oligonucleotide from which a primer extension product can be synthesized under suitable conditions. In certain embodiments, such suitable conditions comprise the primer being hybridized to a complementary nucleic acid and incubated in the presence of, for example, nucleotides, a polymerization-inducing agent, such as a DNA or RNA polymerase, at suitable temperature, pH, metal concentration, salt concentration, etc. In various embodiments, primers are 5 to 100 nucleotides long. In various embodiments, primers are 8 to 75, 10 to 60, 10 to 50, 10 to 40, or 10 to 35 nucleotides long.

The term "ligation" as used herein refers to the covalent joining of two polynucleotide ends. In various embodiments, ligation involves the covalent joining of a 3' end of a first polynucleotide to a 5' end of a second polynucleotide. In various embodiments, ligation results in a phosphodiester bond being formed between the polynucleotide ends. In various embodiments, ligation may be mediated by any enzyme, chemical, or process that results in a covalent joining of the polynucleotide ends. In certain embodiments, ligation is mediated by a ligase enzyme.

The term "analyte" as used herein refers to a substance to be detected using one or more proximity detection probes. Such substances include, but are not limited to, proteins, peptides, antibodies, carbohydrates, hormones, small molecules, cells, microorganisms, and any other substance for which an analyte binding moiety can be developed. An analyte is not a nucleic acid.

The term "target nucleic acid" as used herein refers to an RNA or DNA that has been selected for detection. Exemplary RNAs include, but are not limited to, mRNAs, tRNAs, snRNAs, rRNAs, retroviruses, small non-coding RNAs, microRNAs, polysomal RNAs, pre-mRNAs, intronic RNA, and viral RNA. Exemplary DNAs include, but are not limited to, genomic DNA, plasmid DNA, phage DNA, nucleolar DNA, mitochondrial DNA, chloroplast DNA, cDNA, synthetic DNA, yeast artificial chromosomal DNA ("YAC"), bacterial artificial chromosome DNA ("BAC"), other extrachromosomal DNA, and primer extension products. Exemplary methods for detecting short nucleic acids, e.g., using stem-loop primers and/or short primers, can be found, e.g., in U.S. Patent Publication No. US 2005/0266418 to Chen et al., and U.S. Patent Publication No. US 2006/0057595 to Lao et al.

The term "multifunctional lysis buffer" as used herein refers to a buffer that is capable of lysing, homogenizing, and/or extracting a selected biological sample without substantially degrading the target nucleic acid, and while maintaining adequate analyte structure such that a proximity detection probe is able to bind the analyte in the lysate. In various embodiments, less than 1%, less than 5%, less than 10%, less than 15%, less than 20%, less than 25%, less than 30%, or less than 50% of the target nucleic acid is degraded. In various embodiments, at least 99%, at least 95%, at least 90%, at least 85%, at least 80%, at least 75%, at least 70%, or at least 50% of the target analyte retains adequate structure such that a proximity detection probe is able to bind the analyte in the lysate.

In various embodiments, a multifunctional lysis buffer is compatible with the methods described herein, under appropriate temperature and dilution conditions for carrying out the methods. In certain embodiments, a multifunctional lysis buffer comprises at least one chemical selected from NDSB-201 (3-(1-pyridino)-1-propane sulfonate), LDAO (lauryldimethylamine-oxide), CHAPS (3-[(3-cholamidopropyl)dimethylammonio]-1-propanesulfonate), DEDTAB (dodecylethyldimethylammonium bromide), Zwittergent 3-10 (n-decyl-N,N-dimethyl-3-ammonio-1-propane-sulfonate), and CAPSO (3-(cyclohexylamino)-2-hydroxy-1-propanesulfonic acid).

The term "biological sample" as used herein refers to any sample that is suspected of containing a target analyte and/or a target nucleic acid. Exemplary biological samples include, but are not limited to, prokaryotic cells, eukaryotic cells, tissue samples, viral particles, bacteriophage, infectious particles, pathogens, fungi, food samples, bodily fluids (including, but not limited to, mucus, blood, plasma, serum, urine, saliva, and semen), water samples, and filtrates from, e.g., water and air.

A "proximity detection probe" as used herein, is a probe that comprises at least one analyte binding moiety connected, either covalently or noncovalently, to at least one oligonucleotide moiety. In certain embodiments, the oligonucleotide moiety comprises a first member of a binding pair and the analyte binding moeity comprises a second member of a binding pair, wherein the first member of the binding pair and the second member of the binding pair are capable of stably associating under the conditions used for proximity detection probe binding and hybridization and/or ligation. In various embodiments, one skilled in the art can select an appropriate binding pair. In certain embodiments, a proximity detection probe comprises one or more linkers connecting at least one analyte binding moiety to at least one oligonucleotide moiety. In various embodiments, one skilled in the art can select an appropriate linker.

An "analyte binding moiety" as used herein, refers to a moiety that binds to a target analyte. Exemplary moieties that may be used as analyte binding moieties include, but are not limited to, monoclonal antibodies and fragments thereof that are capable of binding an analyte, polyclonal antibodies and fragments thereof that are capable of binding an analyte, proteins, peptides, lectins, nucleic acids, aptamers, carbohydrates, soluble cell surface receptors, small molecules, and any other binding moieties that are specific for a target analyte.

The term "proximity detection assay" or "PDA" as used herein refers to an assay that involves contacting an analyte with at least two proximity detection probes, wherein each probe comprises an analyte binding moiety and an oligonucleotide moiety. The analyte binding moiety of each probe may be the same or different. The oligonucleotide moiety of each probe may be the same or different. In certain embodiments, the analyte is contacted with a set of proximity detection probes. In various embodiments, a set of proximity detection probes comprises 2, 3, 4, 5, or more than 5 proximity detection probes. In certain embodiments, a set of proximity detection probes is a pair of proximity detection probes, or a "proximity detection probe pair." In certain embodiments, the analyte binding moiety of each probe in a set of proximity detection probes is different. In certain embodiments, the analyte binding moiety of each probe in a set of proximity detection probes is capable of binding to a different epitope within the analyte. As used herein, different epitopes may be overlapping epitopes or non-overlapping epitopes in the analyte sequence and/or in three-dimensional space. In certain embodiments, the oligonucleotide moiety of each probe in a set of proximity detection probes comprises a different sequence.

In various embodiments, after contacting an analyte with at least two proximity detection probes, the oligonucleotide moieties of at least two of the proximity detection probes are capable of interacting with one another. In various embodiments, such interaction may be mediated by one or more additional oligonucleotides. In certain embodiments, at least a portion of the oligonucleotide moieties of at least two of the proximity detection probes hybridize to one another. In certain embodiments, at least a portion of each of the oligonucleotide moieties of the proximity detection probes hybridizes to another oligonucleotide. For example, in certain embodiments, at least one additional oligonucleotide is added (referred to herein as a "splint oligonucleotide"), which mediates the interaction between at least two proximity detection probes by hybridizing to at least a portion of the oligonucleotide moiety of each of the proximity detection probes. A proximity detection assay (PDA) in which the oligonucleotide moieties hybridize to one another, or hybridize to another oligonucleotide that forms a bridge between at least two oligonucleotide moieties, wherein the oligonucleotide moieties are not ligated to one another, may also be referred to as a "proximity interaction assay" or "PIA."

In certain embodiments, the oligonucleotide moieties of at least two of the proximity detection probes are capable of being ligated together by a polynucleotide ligase enzyme. In certain embodiments, the ligatable ends of each of the oligonucleotide moieties are brought together by at least one other oligonucleotide (also called a "splint oligonucleotide") that is capable of hybridizing to at least a portion of the oligonucleotide moiety of each proximity detection probe. A proximity detection assay (PDA) in which oligonucleotide moieties of the proximity detection probes are ligated together may also be referred to as a "proximity ligation assay" or "PLA".

In various embodiments, following hybridization and/or ligation of the oligonucleotide moieties of at least two proximity detection probes, the hybridized and/or ligated oligonucleotide moieties may be detected by any method known in the art. Exemplary means of detecting the hybridized and/or ligated oligonucleotide moieties include, but are not limited to, direct detection, real-time PCR (including, but not limited to, 5'-nuclease real-time PCR), rolling circle amplification, combinations of ligation and PCR, and pre-amplification followed by a detection step (such as, but not limited to, a second amplification, direct detection, ligation, etc.). Certain exemplary methods of detecting nucleic acids are described herein.

Exemplary proximity detection assays are described, e.g., in U.S. Pat. No. 6,511,809 B2; U.S. Patent Publication No. US 2002/0064779; PCT Publication No. WO 2005/123963; and Gustafsdottir et al., *Clin. Chem.* 52: 1152-1160 (2006).

The term "quantitative nucleic acid detection assay" as used herein refers to an assay that is capable of quantitating the amount of a particular nucleic acid sequence in a sample. Certain exemplary quantitative nucleic acid detection assays are described herein in the section entitled "Certain Exemplary Methods."

As used herein, the term "detector probe" refers to a molecule used in an amplification reaction that facilitates detection of the amplification product. Exemplary amplification reactions include, but are not limited to, quantitative PCT, real-time PCR, and end-point analysis amplification reactions. In various embodiments, such detector probes can be used to monitor the amplification of a target nucleic acid and/or control nucleic acid. In various embodiments, detector probes present in an amplification reaction are suitable for monitoring the amount of amplicon(s) produced as a function of time.

In various embodiments, a detector probe is "sequence-based," meaning that it detects an amplification product in a sequence-specific manner. As a non-limiting example, a sequence-based detector probe may comprise an oligonucleotide that is capable of hybridizing to a specific amplification product. In certain embodiments, a detector probe is "sequence-independent," meaning that it detects an amplification product regardless of the sequence of the amplification product.

Certain exemplary detector probes include, but are not limited to, probes used in a 5'-nuclease assay (for example, TaqMan® probes, described, e.g., in U.S. Pat. No. 5,538,848); stem-loop molecular beacons (see, e.g., U.S. Pat. Nos. 6,103,476 and 5,925,517 and Tyagi and Kramer, 1996, *Nature Biotechnology* 14:303-308); stemless or linear beacons (see, e.g., WO 99/21881), PNA Molecular Beacons™ (see, e.g., U.S. Pat. Nos. 6,355,421 and 6,593,091); linear PNA beacons (see, e.g., Kubista et al., 2001, SPIE 4264:53-58); non-FRET probes (see, e.g., U.S. Pat. No. 6,150,097); Sunrise®/Amplifluor® probes (U.S. Pat. No. 6,548,250); stem-loop and duplex Scorpion™ probes (Solinas et al., 2001, Nucleic Acids Research 29:E96 and U.S. Pat. No. 6,589,743); bulge loop probes (U.S. Pat. No. 6,590,091); pseudo knot probes (U.S. Pat. No. 6,589,250), cyclicons (U.S. Pat. No. 6,383,752); MGB Eclipse™ probe (Epoch Biosciences); hairpin probes (U.S. Pat. No. 6,596,490); peptide nucleic acid (PNA) light-up probes; self-assembled nanoparticle probes; and ferrocene-modified probes. Certain exemplary detector probes are described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161.

In various embodiments, detector probes can comprise quenchers. Exemplary quenchers include, but are not limited to, black hole quenchers (Biosearch), Iowa Black (IDT), QSY quencher (Molecular Probes), and Dabsyl and Dabcel sulfonate/carboxylate Quenchers (Epoch). In certain embodiments, detector probes may comprise two probes, wherein, for example, one probe comprises a fluorescent moiety and another probe comprises a quencher, wherein hybridization of the two probes together on a target quenches the signal, or wherein hybridization of the two probes on a target alters the signal via a change in fluorescence. Certain exemplary detector probes comprising two probes are described, e.g., in U.S. Patent Publication No. US 2006/0014191 to Lao et al. Certain exemplary detector probes also include, but are not limited to, sulfonate derivatives of fluorescenin dyes with $SO_3$ instead of the carboxylate group, phosphoramidite forms of fluorescein, and phosphoramidite forms of CY 5 (commercially available, e.g., from Amersham).

In certain embodiments, detector probes comprise intercalating labels. Examplary intercalating labels include, but are not limited to, ethidium bromide, SYBR® Green I (Molecular Probes), and PicoGreen® (Molecular Probes), which allowing visualization in real-time, or end point, of an amplification product in the absence of a nucleic acid probe. In certain embodiments, a detector probe comprising an intercalating label is a sequence-independent detector probe. In certain embodiments, real-time visualization can comprise a sequence-independent intercalating detector probe and a sequence-based detector probe.

In certain embodiments, a detector probe is at least partially quenched when not hybridized to a complementary sequence in the amplification reaction, and is at least partially unquenched when hybridized to a complementary sequence in the amplification reaction. In various embodiments, detector probes can further comprise various modifications, such as, for example, a minor groove binder (see, e.g., U.S. Pat. No. 6,486,308) to further provide desirable thermodynamic characteristics. In certain embodiments, detector probes can correspond to identifying portions or identifying portion complements, also referred to as zip-codes. Identifying portions are described, e.g., in U.S. Pat. Nos. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein).

Detector probes may be "detectably different", which means that they are distinguishable from one another by at least one detection method. Detectably different detector probes include, but are not limited to, detector probes that emit light of different wavelengths, detector probes that absorb light of different wavelengths, detector probes that scatter light of different wavelengths, detector probes that have different fluorescent decay lifetimes, detector probes that have different spectral signatures, detector probes that have different radioactive decay properties, detector probes of different charge, and detector probes of different size. In certain embodiments, a detector probe emits a fluorescent signal.

"Endpoint polymerase chain reaction" or "endpoint PCR" is a polymerase chain reaction method in which the presence or quantity of nucleic acid target sequence is detected after the PCR reaction is complete, and not while the reaction is ongoing.

"Real-time polymerase chain reaction" or "real-time PCR" is a polymerase chain reaction method in which the presence or quantity of nucleic acid target sequence is detected while the reaction is ongoing. In certain embodiments, the signal emitted by one or more probes present in a reaction composition is monitored during each cycle of the polymerase chain reaction as an indicator of synthesis of a primer extension product. In certain embodiments, fluorescence emitted during each cycle of the polymerase chain reaction is monitored as an indicator of synthesis of a primer extension product.

A "multiplex amplification reaction" is an amplification reaction in which two or more target nucleic acid sequences are amplified in the same reaction. A "multiplex polymerase chain reaction" or "multiplex PCR" is a polymerase chain reaction method in which two or more target nucleic acid sequences are amplified in the same reaction.

A "singleplex amplification reaction" is an amplification reaction in which only one target nucleic acid sequence is amplified in the reaction. A "singleplex polymerase chain reaction" or "singleplex PCR" is a polymerase chain reaction method in which only one target nucleic acid sequence is amplified in the reaction.

"Threshold cycle" or "$C_T$" is defined as the cycle number at which the observed signal from a quantitative nucleic acid detection assay exceeds a fixed threshold. In certain embodiments, the fixed threshold is set as the amount of signal observed in a reaction lacking a target nucleic acid sequence. In certain embodiments, the fixed threshold is set at a level above the background noise signal. For example, in certain embodiments, the fixed threshold is set at a value corresponding to 3 or more times the combination of the root mean squared of the background noise signal and the background noise signal. In certain embodiments, the observed signal is from a fluorescent label.

The term "normalizer control" means a molecule present in a biological sample and/or a lysate of a biological sample that can be used to normalize the amount of a target analyte and/or a target nucleic acid detected in a proximity detection assay. In certain embodiments, a normalizer control is an analyte. In certain embodiments, a normalizer control is a nucleic acid.

A normalizer control may, in various embodiments, be referred to as "exogenous" or "endogenous." In certain embodiments, an exogenous normalizer control is added to a biological sample after it was collected. In certain embodiments, an exogenous normalizer control has been added to a lysate of a biological sample. In various embodiments, the biological sample and/or the lysate of the biological sample naturally comprises an amount of the same analyte and/or nucleic acid that is used as an exogenous normalizer control, but the normalizer control is considered to be exogenous because an additional amount of analyte and/or nucleic acid has been added.

In certain embodiments, an endogenous normalizer control is already present in a biological sample at the time the sample is collected for analysis. In certain embodiments, an endogenous normalizer control is present in a lysate of a biological sample without having been added to the lysate. A normalizer control is referred to as "housekeeping," in certain embodiments, when it is present at a high level in a biological sample and/or a lysate of a biological sample without having been added. In certain embodiments, a housekeeping normalizer control is present at a high level in more than one different type of biological sample.

In certain embodiments, a normalizer control is an endogenous analyte. In certain embodiments, a normalizer control is an endogenous protein. In certain embodiments, a normalizer controls is an endogenous housekeeping protein. Certain exemplary endogenous housekeeping protein normalizer controls include, but are not limited to, GAPDH, acidic ribosomal protein, beta-actin, HPRT, beta-glucuronidase, cystatin B, ICAM1, and p53.

In certain embodiments, a normalizer control is an exogenous analyte. In certain embodiments, a normalizer control is an exogenous protein. Certain exemplary exogenous protein normalizer controls include, but are not limited to, bacterial proteins, protein tags, viral proteins, intact virions, insect proteins, mammalian proteins not normally expressed in the selected biological sample, and mammalian proteins normally expressed at a low level in the selected biological sample. Certain exemplary bacterial proteins that may be used as exogenous protein normalizer controls include, but are not limited to, β-galactosidase and chloroamphenicol acetyltransferase (CAT). Certain exemplary protein tags that may be used as exogenous protein normalizer controls include, but are not limited to, histidine tags (e.g., $His_6$ tags), flu tags, hemagglutinin tags, glutathione-s-transferase tags, c-myc tags, and luciferase. In certain embodiments, an exogenous protein normalizer comprises a protein tag fused to another protein.

In certain embodiments, a normalizer control is an endogenous nucleic acid. In certain embodiments, a normalizer control is an endogenous stretch of genomic DNA. In certain embodiments, the endogenous stretch of genomic DNA comprises at least a portion of a single-copy gene. In certain embodiments, the endogenous stretch of genomic DNA comprises at least a portion of a gene that is present in the genome in more than one copy. Certain exemplary endogenous single-copy genomic DNA normalizer controls include, but are not limited to, at least a portion of the RNase P gene and at least a portion of a short tandem repeat (STR) locus. Certain exemplary STR loci include, but are not limited to, D3S1358, HUMTH01, D21S11, D18S51, G475, Amelogenin, HUMvWFA31, D8S1179, HUMTPOX, HUMFIBRA, D5S818, D7S820, D13S317, D16S539, HUMCSF1PO, and S159. Certain STR loci are described, e.g., in U.S. Pat. No. 7,008,771.

In certain embodiments, a normalizer control is an endogenous RNA. In certain embodiments, a normalizer control is an endogenous housekeeping RNA. Certain exemplary endogenous housekeeping RNA normalizer controls include, but are not limited to, GAPDH, 18S, beta-actin, acidic ribosomal protein, HPRT, beta-glucuronidase, cystatin B, ICAM1 and p53. In certain embodiments, a normalizer control is an endogenous mRNA that encodes at least one target analyte to be detected.

In various embodiments, a normalizer control is an exogenous nucleic acid. In various embodiments, an exogenous nucleic acid comprises an RNA and/or a DNA. Exemplary RNAs include, but are not limited to, mRNAs, tRNAs, snRNAs, rRNAs, retroviruses, small non-coding RNAs, microRNAs, polysomal RNAs, pre-mRNAs, intronic RNA, and viral RNA. Exemplary DNAs include, but are not limited to, genomic DNA, plasmid DNA, phage DNA, nucleolar DNA, mitochondrial DNA, chloroplast DNA, cDNA, synthetic DNA, yeast artificial chromosomal DNA ("YAC"), bacterial artificial chromosome DNA ("BAC"), other extrachromosomal DNA, and primer extension products. In certain embodiments, an exogenous nucleic acid comprises PNA. In certain embodiments, an exogenous nucleic acid comprises a sequence normally found in an organism other than the organism from which the biological sample was collected. In certain embodiments, an exogenous nucleic acid comprises a sequence normally found in the organism from which the biological sample was collected. In certain embodiments, an exogenous normalizer control comprises a sequence that is not normally found in a known organism. In certain embodiments, an exogenous normalizer control comprises a sequence that is normally found in one type of nucleic acid (for example, mRNA) but the exogenous normalizer control comprises that sequence in another type of nucleic acid (for example, DNA). In certain embodiments, an exogenous nucleic acid normalizer control is TaqMan® Exogenous Internal Positive Control Reagent (Applied Biosystems catalog #4308323).

In various embodiments, the amount of a target nucleic acid may be normalized to a normalizer control using the "delta $C_T$ method" or "$\Delta C_T$ method," which involves calculating the $\Delta C_T$. In certain embodiments, the $\Delta C_T$ is calculated by subtracting the $C_T$ of a quantitative nucleic acid detection assay used to detect a normalizer control from the $C_T$ of a quantitative nucleic acid detection assay used to detect a target nucleic acid. In certain embodiments, the fold difference in the amounts of the normalizer control and target nucleic acid is calculated from the $\Delta C_T$. In certain embodiments, the fold difference in the amounts of the normalizer control and target nucleic acid is calculated from the $\Delta C_T$ according to the formula $2^{-\Delta C_T}$.

In various embodiments, the amount of a target analyte may be normalized to a normalizer control using the "delta $C_T$ method" or "$\Delta C_T$ method," which involves calculating the $\Delta C_T$. In certain embodiments, the $\Delta C_T$ is calculated by subtracting the $C_T$ of a quantitative nucleic acid detection assay used to detect a normalizer control from the $C_T$ of a quantitative nucleic acid detection assay used to detect a target analyte. In certain embodiments, the fold difference in the amounts of the normalizer control and target analyte is calculated from the $\Delta C_T$. In certain embodiments, the fold difference in the amounts of the normalizer control and target analyte is calculated from the $\Delta C_T$ according to the formula $2^{-\Delta C_T}$.

In various embodiments, the amount of a target nucleic acid may be normalized to a normalizer control using the "comparative $C_T$ method" or "$\Delta\Delta C_T$ method," which involves calculating the $\Delta\Delta C_T$. In various embodiments, the amount of a target analyte may be normalized to a normalizer control using the "comparative $C_T$ method" or "$\Delta\Delta C_T$ method," which involves calculating the $\Delta\Delta C_T$. In certain embodiments, the $\Delta\Delta C_T$ is calculated by subtracting the $\Delta C_T$ of a "calibrator lysate" from the $\Delta C_T$ of a "test lysate." Certain exemplary calibrator lysates include, but are not limited to, a lysate prepared from untreated cells and a lysate prepared from a particular tissue. Certain exemplary test lysates include, but are not limited to, a lysate prepared from treated cells and a lysate prepared from a tissue other than the tissue from which a calibrator lysate was prepared. In certain embodiments, the $\Delta\Delta C_T$ is calculated by subtracting the $\Delta C_T$ of a calibrator lysate from the $\Delta C_T$ of a test lysate.

In certain embodiments, the fold difference in the amount of target nucleic acid in the calibrator and test lysates is calculated from the $\Delta\Delta C_T$ according to the formula $2^{-\Delta\Delta C_T}$. In certain embodiments, the fold difference in the amount of target analyte in the calibrator and test lysates is calculated from the $\Delta\Delta C_T$ according to the formula $2^{-\Delta\Delta C_T}$. Use of the $\Delta\Delta C_T$ method is described, e.g., in Applied Biosystems, "Guide to Performing Relative Quantitation of Gene Expression Using Real-Time Quantitative PCR"; and Applied Biosystems, User Bulletin #2: ABI Prism 7700 Sequence Detection System, (Dec. 11, 1997 (updated October 2001)).

The term "blocking agent" means a substance included in a reaction to reduce non-specific interactions. In certain embodiments, a blocking agent is included in a reaction to reduce non-specific interactions involving analytes. In certain embodiments, a blocking agent is included in a reaction to reduce non-specific interactions involving nucleic acids.

In certain embodiments, a blocking agent is an analyte. A blocking agent that is an analyte may be referred to as an "analyte blocking agent." In certain embodiments, a blocking agent is a protein. A blocking agent that is a protein may be referred to as a "protein blocking agent." Certain exemplary protein blocking agents include, but are not limited to, BSA, casein, random peptide library fragments, preparations of mammalian IgG fractions, and non-fat dry milk. In certain embodiments, a blocking agent is a gelatin. A blocking agent that is a gelatin may be referred to as a "gelatin blocking agent." Certain exemplary gelatin blocking agents include, but are not limited to, fish-derived gelatin (including, but not limited to, cold fish gelatin (Sigma # G7765)), bovine-derived gelatin, and porcine-derived gelatin. In certain embodiments, an analyte blocking agent is included in a reaction at a concentration of 0.01 to 5%. In certain embodiments, an analyte blocking agent is included in a reaction at a concentration of 0.01 to 2%. In certain embodiments, an analyte blocking agent is present in a multifunctional lysis buffer at a concentration of from 0.05 to 0.5%. Certain exemplary blocking agents are described, e.g., in Vogt et al., *J. Immunol. Meth.*, 101(1): 43-5 (1987).

In certain embodiments, a blocking agent is a nucleic acid. A blocking agent that is a nucleic acid may be referred to as a "nucleic acid blocking agent." In various embodiments, a blocking agent comprises RNA and/or DNA. In various embodiments, a blocking agent comprises single-stranded and/or double-stranded nucleic acids. In certain embodiments, a blocking agent comprises predominantly single-stranded nucleic acid. A blocking agent that is predominantly single-stranded nucleic acid may be referred to as a "single-stranded nucleic acid blocking agent." In certain embodiments, a blocking agent comprises predominantly double-stranded nucleic acid. A blocking agent that is predominantly double-stranded nucleic acid may be referred to as a "double-stranded nucleic acid blocking agent." Certain exemplary single-stranded nucleic acid blocking agents include, but are not limited to, polyA and polydC. Certain exemplary double-stranded nucleic acid blocking agents include, but are not limited to, genomic DNA, sheared genomic DNA, polydC+ polydG, and polydI+polydC. Certain exemplary sheared genomic DNAs include, but are not limited to, sheared salmon sperm DNA and sheared calf thymus DNA.

Certain Exemplary Reagents

Certain Exemplary Proximity Detection Probes

A proximity detection probe comprises at least one analyte binding moiety and at least one oligonucleotide moiety. An analyte binding moiety is capable of binding to a selected analyte. In certain embodiments, a proximity detection probe comprises one analyte binding moiety and one oligonucleotide moiety. In certain embodiments, a proximity detection probe comprises more than one analyte binding moiety. In certain embodiments, a proximity detection probe comprises more than one oligonucleotide moiety. Certain exemplary multivalent proximity probes are described, e.g., in U.S. Patent Publication No. US 2005/0003361 A1 to Fredriksson.

In various embodiments, the oligonucleotide moiety of a proximity detection probe may comprise one or more of ribonucleotides, deoxyribonucleotides, analogs of ribonucleotides, and analogs deoxyribonucleotides. Exemplary analogs of ribonucleotides and analogs of deoxyribonucleotides include, but are not limited to, analogs that comprise one or more modifications to the nucleotide sugar, phosphate, and/or base moiety. Exemplary oligonucleotide analogs include, but are not limited to, LNA (see, e.g., U.S. Pat. No. 6,316,198), PNA (see, e.g., U.S. Pat. No. 6,451,968), and any other nucleotide analogs discussed herein or known in the art (see, e.g., Loakes, *Nucleic Acids Res.* 2001 June 15; 29(12):2437-47, and Karkare et al., *Appi Microbiol Biotechnol.* 2006 August; 71(5):575-86. Epub 2006 May 9).

In various embodiments, the oligonucleotide moeity of the proximity detection probe may comprise at least 10, at least 15, at least 20, at least 25, at least 30, at least 35, at least 40, at least 50, at least 60, at least 75, or at least 100 nucleotides. In various embodiments, the oligonucleotide moeity of the proximity detection probe may comprise 10 to 1000 nucleotides. In various embodiments, the oligonucleotide moeity may comprise 10 to 500 nucleotides. In various embodiments, the oligonucleotide moeity may comprise 10 to 200 nucleotides. In various embodiments, the oligonucleotide moeity may comprise 10 to 100 nucleotides.

The oligonucleotide moiety and the analyte binding moiety of the proximity detection probe may be covalently or non-covalently associated with one another. Certain ways of covalently and non-covalently associating an analyte binding moiety and an oligonucleotide moiety are known in the art.

In certain embodiments, the oligonucleotide moiety comprises a first member of a binding pair and the analyte binding moiety comprises a second member of a binding pair, wherein the first member of the binding pair and the second member of the binding pair are capable of stably associating under the conditions used for proximity detection probe binding and hybridization and/or ligation. In certain embodiments, the binding pair need not stably associate during detection of the hybridized and/or ligated oligonucleotide moieties. Certain exemplary binding pairs include, but are not limited to, antibody/antigen, biotin/avidin, biotin/streptavidin, hybridizing nucleic acids, receptor/ligand, folic acid/folate binding protein, vitamin B12/intrinsic factor, protein A/Fc, and protein G/Fc, metal/chelator, etc. In certain embodiments, streptavidin may be attached to an oligonucleotide moiety by the use of a sulfo-SMCC reagent (see, e.g., Pierce Catalog #22322). In certain embodiments, the analyte binding moiety and the oligonucleotide moiety of the proximity detection probe are covalently associated. Certain methods of forming covalent bonds between various molecules are known in the art and can be found, e.g., in the Pierce Catalog. Certain exemplary methods of making proximity detection probes are described, e.g., in Gullberg et. al., *Proc. Natl. Acad. Sci.* 101(22): 8420-8424 (2004).

In various embodiments, the 3' end or the 5' end of the oligonucleotide moiety is associated with the analyte binding moiety. In certain embodiments, the oligonucleotide moeity is associated with the analyte binding moiety at a location other than the 3' end or the 5' end of the oligonucleotide moiety, for example, through one or more nucleotides or modified nucleotides in the oligonucleotide sequence.

In various embodiments, two or more proximity detection probes are combined to form a proximity detection probe set. In various embodiments, a first proximity detection probe is paired with a second proximity detection probe to form a proximity detection probe pair. The proximity detection probes of a proximity detection probe set may each bind to the same or different analytes. In certain embodiments, the proximity detection probes in a set each bind to the same analyte. In certain embodiments, the proximity detection probes in a set each bind to different analytes. In certain embodiments, a first subset of proximity detection probes in a set each bind to a first analyte and a second subset of proximity detection probes in a set each bind to a second analyte. In certain embodiments, a first subset of proximity detection probes in a set binds to a first analyte, and a second subset of proximity detection probes in a set binds to a second analyte, wherein the first and second analytes are capable of associating with one another under certain conditions. In various embodiments, such a proximity detection probe set may, for example, be used to detect the association of the first and second analytes under certain conditions.

In certain embodiments, a proximity detection probe is capable of binding to more than one analyte, either through the same analyte binding moiety, or through multiple analyte binding moieties of the proximity detection probe. In certain embodiments, a proximity detection probe is capable of binding to two or more members of a family of related analytes.

In various embodiments, at least a portion of the oligonucleotide moiety of a first member of a proximity detection probe set is capable of hybridizing to at least a portion of the oligonucleotide moiety of a second member of a proximity detection probe set. In various embodiments, the hybridized region comprises at least 5 base pairs, at least 10 base pairs, at least 15 base pairs, at least 20 base pairs, at least 25 base pairs, at least 30 base pairs, at least 40 base pairs, at least 50 base pairs, at least 75 base pairs, or at least 100 base pairs.

In various embodiments, the oligonucleotide moiety of a first member of a proximity detection probe set is not capable of hybridizing to the oligonucleotide moiety of a second member of a proximity detection probe set. For example, in certain embodiments, at least one splint oligonucleotide may be added to the proximity detection assay, wherein the splint oligonucleotide(s) are capable of hybridizing to at least a portion of the oligonucleotide moiety of the first proximity detection probe, and are also capable of hybridizing to at least a portion of the oligonucleotide moiety of the second proximity detection probe. In various embodiments, the hybridized region between the splint oligonucleotide(s) and an oligonucleotide moiety of a proximity detection probe comprises at least 5 base pairs, at least 10 base pairs, at least 15 base pairs, at least 20 base pairs, at least 25 base pairs, at least 30 base pairs, at least 40 base pairs, at least 50 base pairs, at least 75 base pairs, or at least 100 base pairs. In various embodiments, a splint oligonucleotide is symmetric, e.g., it hybridizes to an equal number of bases of each oligonucleotide moiety. In various embodiments, a splint oligonucleotide is asymmetric, e.g., it hybridizes to a greater number of bases of a first oligonucleotide moiety than of a second oligonucleotide moiety. Certain exemplary asymmetric asymmetric splints are described, e.g., in PCT Publication No. WO 2005/123963.

In various embodiments, a splint oligonucleotide hybridizes to the first and second oligonucleotide moieties in such a way that the 3' end of one of the oligonucleotide moieties is adjacent to the 5' end of the other oligonucleotide moieties. In certain embodiments, the 3' and 5' ends of the oligonucleotide moieties of the proximity detection probe pair are capable of being ligated together. In certain embodiments, the 3' end of one of the oligonucleotide moieties is separated from the 5' end of the other oligonucleotide moieties by a gap of 1 or more nucleotides. In certain embodiments, the gap is filled in using a polymerase such that the filled-in ends are capable of being ligated together.

In various embodiments, a splint oligonucleotide may comprise one or more of ribonucleotides, deoxyribonucleotides, analogs of ribonucleotides, and analogs deoxyribonucleotides. Exemplary analogs of ribonucleotides and analogs of deoxyribonucleotides include, but are not limited to, analogs that comprise one or more modifications to the nucleotide sugar, phosphate, and/or base moiety. Exemplary oligonucleotide analogs include, but are not limited to, LNA (see, e.g., U.S. Pat. No. 6,316,198), PNA (see, e.g., U.S. Pat. No. 6,451,968), and any other nucleotide analogs discussed herein or known in the art (see, e.g., Loakes, *Nucleic Acids Res.* 2001 June 15; 29(12):2437-47, and Karkare et al., *Appl Microbiol Biotechnol.* 2006 August; 71(5):575-86. Epub 2006 May 9). In certain embodiments, a splint oligonucleotide comprises at least one deoxy-uracil (dU) nucleotide in place of at least one deoxy-thymine (dT) nucleotide.

One skilled in the art can select appropriate sequences and lengths for the oligonucleotide moieties of proximity detection probes and/or splint oligonucleotides, according to the intended use. A discussion of exemplary methods of selecting oligonucleotide moieties for proximity detection probes and/or split oligonucleotides can be found, e.g., in U.S. Pat. No. 6,511,809 B2 and PCT Publication No. WO 2005/123963.

Certain Exemplary Multifunctional Lysis Buffers

As discussed above, multifunctional lysis buffers are capable of lysing, homogenizing, and/or extracting a selected biological sample without substantially degrading a target nucleic acid, and while maintaining adequate analyte epitope structure such that a proximity detection probe is able to bind an analyte in the lysate.

In certain embodiments, a multifunctional lysis buffer comprises at least one chemical selected from NDSB-201, LDAO, CHAPS, DEDTAB, Zwittergent 3-10, and CAPSO. In various embodiments, a multifunctional lysis buffer comprises between 0.01% and 20% of at least one chemical selected from NDSB-201, LDAO, CHAPS, DEDTAB, Zwittergent 3-10, and CAPSO. In various embodiments, a multifunctional lysis buffer comprises between 0.05% and 10%, between 0.05% and 5%, between 0.1% and 5%, or between 0.1% and 2%, of at least one chemical selected from NDSB-201, LDAO, CHAPS, DEDTAB, Zwittergent 3-10, and CAPSO. In various embodiments, a multifunctional lysis buffer comprises 0.05%, 0.1%, 0.2%, 0.5%, 1%, 2%, 5%, or 10% of at least one chemical selected from NDSB-201, LDAO, CHAPS, DEDTAB, Zwittergent 3-10, and CAPSO In certain embodiments, a multifunctional lysis buffer comprises one or more additional ingredients suitable for biological buffers. Exemplary additional ingredients include, but are not limited to, buffering agents, divalent cation chelators (such as, for example, EDTA, citrate, and EGTA), monovalent salts, divalent salts, reducing agents, BSA, enzyme inhibitors (such as, for example, phosphatase inhibitors, protease inhibitors, and RNAse inhibitors), nucleic acids (such as, for example, poly A, salmon sperm DNA, etc.), single-stranded DNA binding proteins, etc. In various embodiments, one skilled in the art can select one or more additional ingredients according to the intended application. In certain embodiments, a multifunctional lysis buffer comprises at least one buffering agent and at least one divalent cation chelator. In certain embodiments, a multifunctional lysis buffer comprises at least one buffering agent selected from Tris, Hepes, MOPS, BES, BICINE, CAPS, EPPS, MES, PIPES, TAPS, TES, and TRICINE. In certain embodiments, a multifunctional lysis buffer comprises Tris and EDTA.

In various embodiments, a multifunctional lysis buffer comprises 10 mM to 200 mM or 20 mM to 100 mM of at least one buffering agent.

In various embodiments, a multifunctional lysis buffer may have a pH that is appropriate for the intended use, e.g., that is appropriate for a target nucleic acid and a target analyte. In certain embodiments, the multifunctional lysis buffer has a pH between 5 and 9. In certain embodiments, the multifunctional lysis buffer has a pH between 6 and 8.5. In certain embodiments, the multifunctional lysis buffer has a pH between 6.5 and 8.

Certain exemplary multifunctional lysis buffers comprise NDSB-201, Tris, and EDTA.

Certain Exemplary Proteases

In various embodiments, a lysate is treated with a protease in order to release nucleic acids for analysis. In certain embodiments, a protease is selected based on one or more of the following characteristics: the ease with which the protease can be inactivated, whether the protease requires metal ions for activity, whether the protease requires detergents for activity, whether protease digestion results in a degradation of nucleic acids, and whether the protease releases the target nucleic acid.

In certain embodiments, a protease is selected which can be heat-inactivated. In certain embodiments, a protease is selected which can be chemically-inactivated. Certain exemplary chemicals that can be used to inactivate a protease include, but are not limited to, AEBSF, aprotinin, bestatin, chymostatin, E-64, EDTA, EGTA, leupeptin, pepstatin A, 1,10-phenanthroline, phosphoramidon, and PMSF. In certain embodiments, one or more serine proteases are used in the method. In certain embodiments, one or more proteases are selected from subtilisin carlsberg protease, *streptomyces griseus* protease, and proteinase K. When *streptomyces griseus* protease is selected, in certain embodiments, the protease is heat-inactivated. When proteinase K is selected, in certain embodiments, the protease is chemically inactivated.

In certain embodiments, more than one protease is used in the method. When more than one protease is used, the proteases may be added at the same or different times. In various embodiments, when more than one protease is used, the method may comprise one inactivation step or more than one inactivation step. Furthermore, in various embodiments, the inactivation steps may be the same or different, e.g., one or more inactivation steps may be heat treatment, while one or more inactivation steps may be chemical treatment.

In various embodiments, e.g., when the target analyte is a protein or a peptide, a protease is added after hybridization and/or ligation of the proximity detection probe sets.

Certain Exemplary Methods

Methods provided herein may be carried out in any order of the recited events that is logically possible, as well as the recited order of events.

Standard techniques may be used for recombinant DNA, oligonucleotide synthesis, and tissue culture. Enzymatic reactions and purification techniques may be performed according to manufacturer's specifications and/or as commonly accomplished in the art and/or as described herein. The foregoing techniques and procedures may be generally performed according to conventional methods known in the art and as described in various general and more specific references, including but not limited to, those that are cited and discussed throughout the present specification. See, e.g., Sambrook et al. Molecular Cloning: A Laboratory Manual (2d ed., Cold Spring Harbor Laboratory Press, Cold Spring Harbor, N.Y. (1989)); Lehninger, Biochemistry (Worth Publishers, Inc.); Methods in Enzymology (S. Colowick and N. Kaplan Eds., Academic Press, Inc.); Oligonucleotide Synthesis (N. Gait, ed., 1984); A Practical Guide to Molecular Cloning ($2^{nd}$ Ed., Wily Press, 1988). Unless specific definitions are provided, the nomenclatures utilized in connection with, and the laboratory procedures and techniques of, biology, biochemistry, analytical chemistry, and synthetic organic chemistry described herein are those known and used in the art.

Methods of detecting a target analyte and a target nucleic acid in a biological sample are provided. In various embodiments, the method permits detection of at least one analyte and at least one target nucleic acid in the same vessel. For example, in various embodiments the processes carried out for detection of the at least one analyte and the processes carried out for detection of the at least one nucleic acid are applied to the same sample. Thus, in various embodiments, the method allows better correlation between the amount of target analyte detected and the amount of target nucleic acid detected, for example, because the sample has not been divided and subjected to different conditions and processes, which may differently affect the efficiency of certain detection methods.

In various embodiments, a method comprises lysing the biological sample, detecting the target analyte using a proximity detection assay, and detecting the target nucleic acid. In various embodiments, the detecting the target analyte and detecting the target nucleic acid are carried out in the same vessel. In various embodiments, one or more proximity detection probe sets and one or more target nucleic acids are detected using the same detection method. In various embodiments, one or more proximity detection probe sets and one or more target nucleic acids are detected simultaneously. In various embodiments, the method does not comprise a nucleic acid purification step prior to detection of the one or more proximity detection probe sets and/or detection of the one or more target nucleic acids. For example, in certain embodiments, a first label is used to detect the proximity detection probe sets and a second label is used to detect the target nucleic acids. In certain embodiments, a different label is used to detect each different proximity detection probe set and each different nucleic acid molecule.

Figure 18:
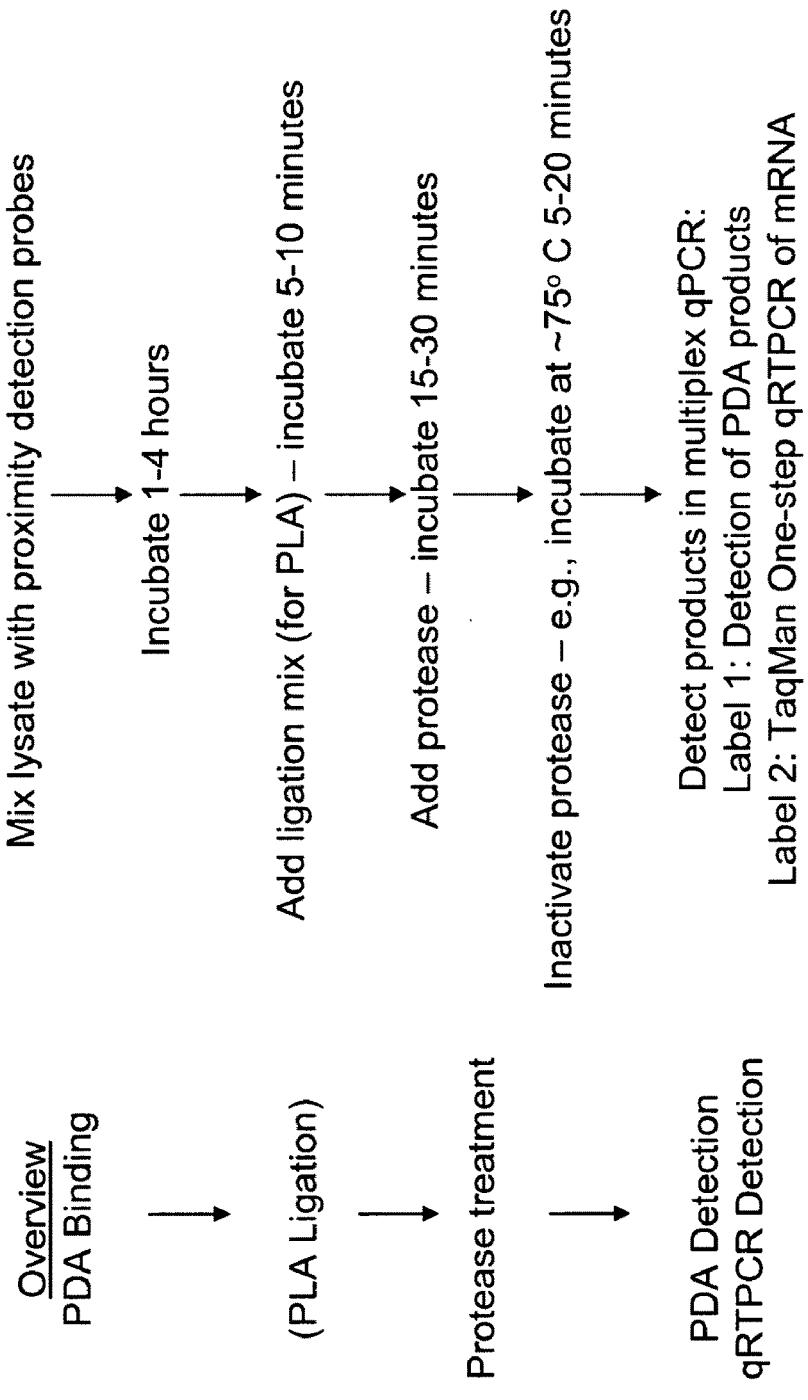
FIG. 18 shows a non-limiting exemplary workflow diagram for certain proximity detection assay/target nucleic acid detection assays described herein. In that workflow design, the PDA products and the mRNA are detected simultaneously in a multiplex amplification reaction.
Figure 19:
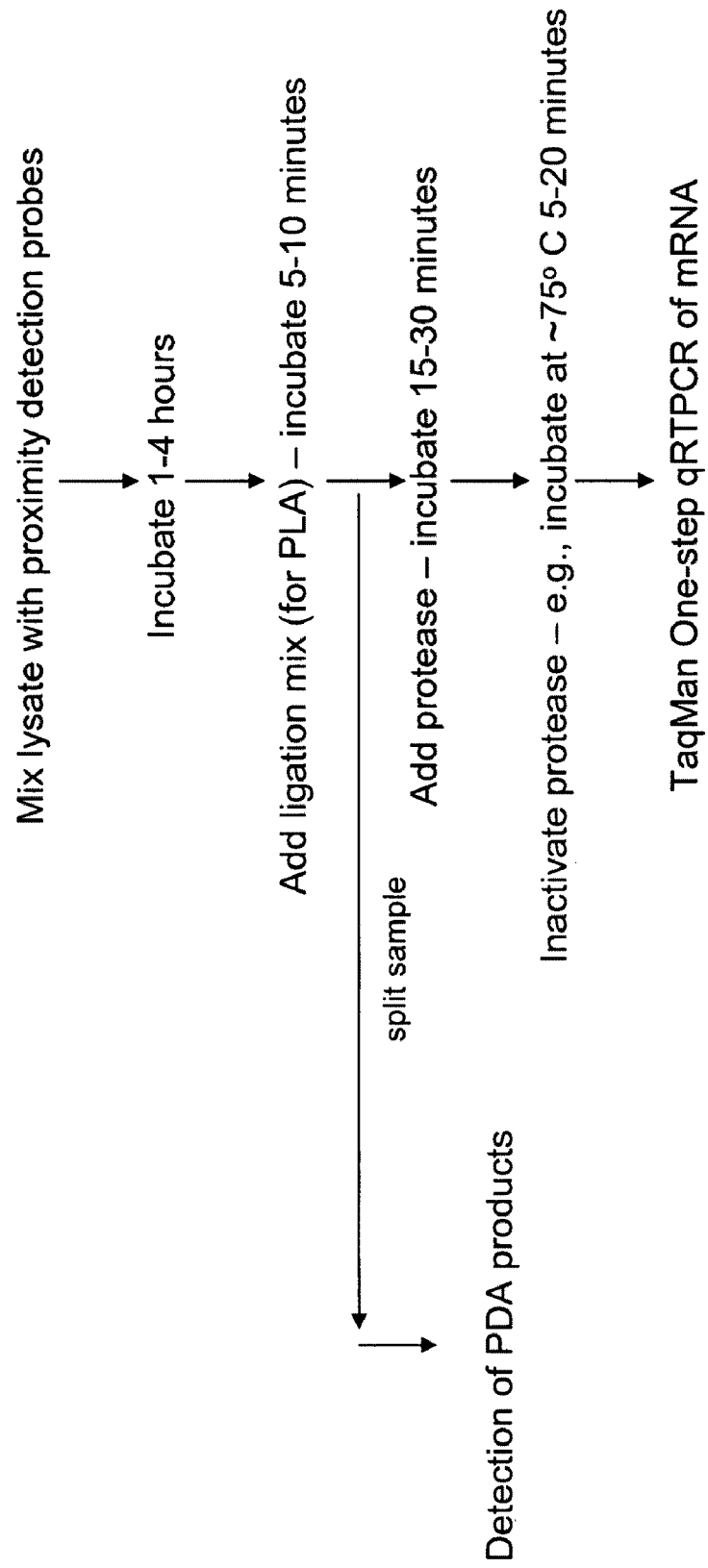
FIG. 19 shows a non-limiting exemplary workflow diagram for certain proximity detection assay/target nucleic acid detection assays described herein. In that workflow design, a sample is removed prior to protease treatment for detection of PDA products, while the remaining sample is protease-treated and used for detection of mRNA.

Certain exemplary workflow diagrams for detecting a target analyte and a target nucleic acid in a biological sample according to certain embodiments are shown in FIGS. 18 and 19.

FIG. 18 shows the following non-limiting exemplary workflow for certain methods. Following lysis, homogenization, and/or extraction of a biological sample in multifunctional lysis buffer, at least one set of proximity detection probes is added to the lysate. The lysate is then incubated under conditions allowing binding of the analyte binding moieties of the proximity detection probes to a target analyte. In various embodiments, the incubation is carried out at a temperature between 0° C. and 45° C. In certain embodiments, the incubation is carried out at greater than 45° C. In various embodiments, the incubation is carried out at a temperature between 0° C. and 10° C., between 4° C. and 15° C., between 4° C. and 30° C., between 10° C. and 20° C., between 15° C. and 30° C., between 20° C. and 30° C., or between 20° C. and 40° C. In various embodiments, the incubation is carried out at 4° C., 10° C., 20° C., 25° C., 30° C., 37° C., or 42° C. In various embodiments, the incubation is carried out for at least overnight. In various embodiments, the incubation is carried out for at least 10 minutes, at least 30 minutes, at least 1 hour, at least 2 hours, at least 3 hours, or at least 4 hours. In various embodiments, the incubation is carried out for 1 to 4 hours.

In various embodiments, at least one splint oligonucleotide is added to the lysate before, at the same time as, or after addition of at least one proximity detection probe set. In various embodiments, a ligation mix is added to the lysate after addition of at least one proximity detection probe set. In certain embodiments, the ligation mix comprises a ligase enzyme suitable for ligating the ends of the oligonucleotide moieties of a proximity detection probe set together, in a suitable buffer. In certain embodiments, the ligation mix is added after addition of at least one splint oligonucleotide. In certain embodiments, the ligation mix is added at the same time as the at least one splint oligonucleotide.

After the ligation mix is added to the lysate, in various embodiments, the lysate is incubated for at least 2 minutes, at least 5 minutes, at least 10 minutes, at least 15 minutes, at least 30 minutes, or at least 1 hour. In certain embodiments, the lysate is incubated for 5 to 10 minutes. In various embodiments, after addition of the ligation mix, the lysate is incubated at a temperature between 0° C. to 25° C. In certain embodiments, the lysate is incubated at a temperature greater than 25° C. In various embodiments, the lysate is incubated at a temperature between 0° C. and 10° C., between 4° C. and 15° C., between 4° C. and 20° C., between 10° C. and 20° C., or between 15° C. and 25° C. In certain embodiments, a ligation reaction is terminated. In certain embodiments, a ligation reaction is terminated by adding at least one protease to the reaction. When a splint oligonucleotide comprises at least one dU nucleotide, in certain embodiments, a ligation reaction is terminated by adding uracil-DNA glycosylase.

In various embodiments, at least one splint oligonucleotide is added to the lysate before, at the same time as, or after at least one proximity detection probe set is added to the lysate. In various embodiments, the ligation step discussed above is omitted. For example, in certain embodiments, where at least one splint oligonucleotide is added after the proximity detection probe set addition and incubation, the lysate is further incubated at a temperature and for a time sufficient to allow hybridization of the at least one splint oligonucleotide to at least one proximity detection probe. In various embodiments, one skilled in the art can select an appropriate time and temperature for such hybridization. In various embodiments, hybridization conditions include temperatures between 0° C. to 75° C. In various embodiments, the incubation is carried out at between 0° C. and 65° C., between 4° C. and 50° C., between 10° C. and 45° C., or between 15° C. and 40° C. In various embodiments, the incubation is carried out at 10° C., 20° C., 25° C., 30° C., 37° C., 42° C., 50° C., 55° C., 60° C., or 65° C. In various embodiments, the incubation is carried out for at least 4 hours. In various embodiments, the incubation is carried out for at least 5 minutes, at least 10 minutes, at least 30 minutes, at least an hour, or at least 2 hours.

In various embodiments, the lysate is treated with at least one protease. In various embodiments, after addition of the at least one protease, the lysate is incubated for at least 5 minutes, at least 10 minutes, at least 15 minutes, at least 30 minutes, at least 1 hour, at least 2 hours, or at least 4 hours. In various embodiments, the lysate is incubated at 0° C. to 65° C. In various embodiments, the lysate is incubated at between 0° C. and 55° C., between 4° C. and 50° C., between 10° C. and 45° C., or between 15° C. and 40° C. In various embodiments, the incubation is carried out at 4° C., 10° C., 20° C., 25° C., 30° C., 37° C., or 42° C. In certain embodiments, at least one protease is inactivated after incubation. In certain embodiments, at least one protease is heat inactivated, e.g., by incubating the lysate for at least 5 minutes at least 50° C. In certain embodiments, the lysate is incubated at least 55° C., at least 60° C., at least 65° C., at least 70° C., or at least 75° C. to heat inactivate the protease. In certain embodiments, at least one protease is inactivated, e.g., by addition of at least one chemical. In certain embodiments, at least one protease is inactivated by addition of PMSF.

In various embodiments, after inactivation of the at least one protease, the target nucleic acid and the hybridized and/or ligated proximity detection probe sets are detected. In various embodiments, detection of the at least one target nucleic acid and the at least one hybridized and/or ligated proximity detection probe sets comprises multiplex quantitative PCR. In certain embodiments, where a target nucleic acid is an RNA, the RNA is reverse transcribed prior to, or as part of, detection.

FIG. 19 shows the following non-limiting exemplary workflow for certain methods. The method shown in FIG. 19 is the same as the method discussed above for FIG. 18, through the ligation step. Prior to protease treatment, however, an aliquot of the lysate is removed for detection of the at least one hybridized and/or ligated proximity detection probe sets.

After removal of the aliquot, the remaining lysate is treated as described above for FIG. 18. The remaining lysate is used for detection of the at least one target nucleic acid, while the removed aliquot is used for detection of the at least one hybridized and/or ligated proximity detection probe sets. In certain embodiments, detection of the at least one target nucleic acid and/or detection of the at least one hybridized and/or ligated proximity detection probe sets comprises quantitative PCR. In certain embodiments, where more than one target nucleic acid and/or more than one hybridized and/or ligated proximity detection probe sets are to be detected, the detection comprises multiplex quantitative PCR. In certain embodiments, where a target nucleic acid is an RNA, the RNA is reverse transcribed prior to, or as part of, detection.

Certain aspects of certain methods will be described in further detail below.

Certain Exemplary Lyses

In various embodiments, the selected biological sample is lysed, homogenized, and/or extracted before the target analytes and target nucleic acids are detected. In certain embodiments, the lysis, homogenization, and/or extraction are carried out in a multifunctional lysis buffer.

Where the selected biological sample is in the form of individual cells, in various embodiments, the cells may be resuspended in multifunctional lysis buffer at a concentration of 100 to 200,000 cells per µl. In various embodiments, the cells are resuspended at a concentration of less than 100 cells per µl or more than 200,000 cells per µl. In various embodiments, the cells are resuspended at a concentration of between 500 and 100,000 cells per µl, between 1,000 and 100,000 cells per µl, between 5,000 and 75,000 cells per µl, or between 10,000 and 75,000 cells per µl. In various embodiments, the cells are resuspended at a concentration of at least 1,000, 2,000, 5,000, 10,000, 15,000, 20,000, 25,000, 30,000, 40,000, or 50,000 cells per µl.

Where the selected biological sample is in the form of tissue, in various embodiments, the tissue may be homogenized into multifunctional lysis buffer such that the concentration of tissue cells that are lysed is roughly equivalent to the concentrations discussed above for individual cells, taking into account the efficiency with which the tissue can be homogenized. For example, in certain embodiments, if 20% of the tissue fails to homogenize, then the remaining 80% is counted for the purposes of determining cell concentration. One skilled in the art can select an appropriate concentration for a tissue sample in multifunctional lysis buffer.

Similarly, where the selected biological sample is in another form, such as a food product, or a water or air filtrate, one skilled in the art can estimate the expected number of cells (e.g., pathogenic agents) in the sample and adjust the volume of multifunctional lysis buffer accordingly. In various embodiments, the selected biological sample may be concentrated by any method known in the art prior to lysis, homogenization and/or extraction with multifunctional lysis buffer.

In various embodiments, following suspension of the selected biological sample in multifunctional lysis buffer, the lysate is physically treated in order to facilitate lysis of the sample. Such physical treatments include, but are not limited to, vortexing, freeze-thaw cycles (e.g., using dry ice, liquid nitrogen, etc.), rotation at a selected temperature, sonication, etc. One skilled in the art can select a suitable physical treatment to facilitate lysis of the selected biological sample.

Following lysis, in certain embodiments, the lysate is centrifuged to pellet solid material. In various embodiments, the cleared lysate may then be removed to a new vessel for storage. In various embodiments, the lysate is stored at 4° C. or frozen, e.g., in a standard freezer, in a −80° C. freezer, or in liquid nitrogen.

Certain Exemplary Proximity Detection Assays

Exemplary proximity detection assays are described, e.g., in U.S. Pat. No. 6,511,809 B2; U.S. Patent Publication No. US 2002/0064779; PCT Publication No. WO 2005/123963; U.S. Patent Publication No. US 2005/0003361 A1; U.S. Patent Publication No. US 2007/0026430; Fredricksson et al., *Nature Biotech.* 20: 473-477 (2002); and Gustafsdottir et al., *Clin. Chem.* 52:1152-1160 (2006).

In various embodiments, a proximity detection assay comprises incubating a biological sample or lysate with at least one proximity detection probe set under conditions allowing interaction between the at least one proximity detection probe set and at least one target analyte. When the proximity detection assay is a proximity ligation assay, in various embodiments, at least one splint oligonucleotide is added to the mixture for each proximity detection probe set and the mixture is incubated under conditions allowing hybridization between the at least one splint oligonucleotide and the oligonucleotide moieties of the proximity detection probe set. In certain embodiments, the splint oligonucleotide hybridizes to two oligonucleotide moieties such that the 3' end of a first oligonucleotide moiety is adjacent to the 5' end of a second oligonucleotide moiety. In certain embodiments, the 3' end of the first oligonucleotide moiety and the 5' end of the second oligonucleotide moiety are ligated together. In certain embodiments, ligation is mediated by a ligase enzyme.

In certain embodiments, the ligated product is detected by at least one method discussed herein. In certain embodiments, the ligated product and the hybridized splint oligonucleotide are subjected to a primer extension reaction as part of, or prior to, the detection method. In certain embodiments, the primer extension reaction produces a double-stranded oligonucleotide. In certain embodiments, the primer extension reaction comprises at least one oligonucleotide primer complimentary to the ligated product. In certain embodiments, the splint oligonucleotide serves as a primer in the primer extension reaction, along with a second oligonucleotide primer. In certain embodiments, two oligonucleotide primers other than the splint oligonucleotide are included in the primer extension reaction. In certain embodiments, following a primer extension reaction that produces a double-stranded oligonucleotide, a first strand of the double stranded oligonucleotide comprises the ligated oligonucleotide moieties, and the second strand comprises the sequence of the splint oligonucleotide connected to (i) a first sequence that is complementary to at least a portion of the first oligonucleotide moiety, and also connected to (ii) a second sequence that is complementary to at least a portion of the second oligonucleotide moiety.

In various embodiments, where the detection method involves hybridization of one or more oligonucleotides (such as, for example, one or more oligonucleotide primers and/or detector probes comprising oligonucleotides), one skilled in the art can select an appropriate nucleotide sequence such that the oligonucleotide can be used to specifically detect the ligated product. For example, in certain embodiments, where the ligated oligonucleotide moieties are subjected to a primer extension reaction, one or more oligonucleotides that hybridize to the primer extension product and not to the oligonucleotide moieties or the splint oligonucleotide can be selected. Such oligonucleotides may be used, in various embodiments, in a direct detection method and/or in a detection method involving an amplification step. In certain embodiments, one or more oligonucleotides can be selected to amplify the ligated oligonucleotide moieties such that amplification will only occur if the moieties are ligated together.

In various embodiments, when the proximity detection assay is a proximity interaction assay, an oligonucleotide moiety of a first proximity detection probe is capable of hybridizing to an oligonucleotide moiety of a second proximity detection probe. Alternatively, in certain embodiments, at least one splint oligonucleotide is added to the mixture for each proximity detection probe set. In various embodiments, the mixture is then incubated under conditions allowing hybridization between the hybridizable oligonucleotide moieties, and/or between the oligonucleotide moieties and the at least one splint oligonucleotide.

In certain embodiments, the hybridized oligonucleotides are subjected to a primer extension reaction as part of, or prior to, the detection method. In certain embodiments, when the oligonucleotide moieties hybridize to one another, the primer extension reaction extends from the end of each oligonucleotide moiety to produce a double-stranded oligonucleotide that comprises a first strand that comprises the first oligonucleotide moiety connected to a sequence that is complementary to at least a portion of the second oligonucleotide moiety, and a second strand that comprises the second oligonucleotide moiety connected to a sequence that is complementary to at least a portion of the first oligonucleotide moiety. In certain embodiments, the double-stranded oligonucleotide is subjected to a further primer extension reaction using at least one oligonucleotide primer. In certain embodiments, the double-stranded oligonucleotide is subjected to a further primer extension reaction using at least two oligonucleotide primers.

In certain embodiments, when at least one splint oligonucleotide hybridizes to the oligonucleotide moieties, the splint oligonucleotide serves as a primer in the primer extension reaction, along with a second oligonucleotide primer, to produce a double-stranded oligonucleotide. In certain embodiments, the double-stranded oligonucleotide comprises a first strand comprising at least a portion of the sequence of each of the oligonucleotide moieties, and a second strand comprising the sequence of the splint oligonucleotide connected to (a sequence that is complementary to at least a portion of one of the oligonucleotide moieties.

In certain embodiments, the hybridized oligonucleotides are detected by at least one method discussed herein. In various embodiments, where the detection method involves hybridization of one or more oligonucleotides (such as, for example, one or more oligonucleotide primers and/or detector probes comprising oligonucleotides), one skilled in the art can select an appropriate nucleotide sequence such that the one or more oligonucleotides can be used to specifically detect the hybridized product. For example, in certain embodiments, where the hybridized oligonucleotide moieties are subjected to a primer extension reaction, one or more oligonucleotides that hybridize to the primer extension product and not to the oligonucleotide moieties can be selected. Such oligonucleotides may be used, in various embodiments, in a direct detection method and/or in a detection method involving an amplification step.

Certain Exemplary Normalizer Controls for Proximity Detection Assays

In various embodiments, the amount of a target nucleic acid may be normalized to at least one normalizer control. In various embodiments, the amount of a target analyte may be normalized to at least one normalizer control. Certain exemplary normalizer controls are described, e.g., herein and in PCT Publication No. WO 2005/123963. In various embodiments, one skilled in the art can select one or more normalizer controls for a particular application.

In various embodiments, a sample comprises at least one normalizer control, at least two normalizer controls, at least three normalizer controls, at least four normalizer controls, or at least five normalizer controls. In certain embodiments, a sample comprises at least one analyte normalizer control and at least one nucleic acid normalizer control. In certain embodiments, a sample comprises at least one endogenous normalizer control and at least one exogenous normalizer control. In certain embodiments, all of the normalizer controls in a sample are endogenous. In certain embodiments, all of the normalizer controls in a sample are exogenous. In certain embodiments, an analyte normalizer control is used to normalize a target analyte. In certain embodiments, a nucleic acid normalizer control is used to normalize a target analyte. In certain embodiments, a nucleic acid normalizer control is used to normalize a target nucleic acid. In certain embodiments, an analyte normalizer control is used to normalize a target nucleic acid. In certain embodiments, a target nucleic acid and a target analyte are normalized to the same normalizer control. In certain embodiments, a target nucleic acid and a target analyte are normalized to different normalizer controls.

In certain embodiments, a normalizer control is detected in the same lysate in which a target analyte and/or a target nucleic acid is detected. In certain embodiments, a normalizer control is detected in the same vessel in which a target analyte and/or a target nucleic acid is detected, using the same or different methods. In various embodiments, the lysate is split or divided and a normalizer control and at least one of a target analyte and a target nucleic acid are detected in separate vessels, using the same or different methods. In various embodiments, a normalizer control is detected at the same time that at least one of a target analyte and a target nucleic acid is detected.

In certain embodiments, the amount of a target analyte may be normalized to a normalizer control using the $\Delta C_T$ method. In certain embodiments, the amount of a target analyte may be normalized to a normalizer control using the $\Delta\Delta C_T$ method. In certain embodiments, the use of a normalizer control may eliminate the need to prepare an external standard curve using an analyte, which may produce a $C_T$ value that differs from the $C_T$ value observed when there is an identical level of the analyte in a lysate.

In certain embodiments, the amount of a target nucleic acid may be normalized to a normalizer control using the $\Delta C_T$ method. In certain embodiments, the amount of a target nucleic acid may be normalized to a normalizer control using the $\Delta\Delta C_T$ method. In certain embodiments, the use of a normalizer control may eliminate the need to prepare an external standard curve using a nucleic acid, which may produce a $C_T$ value that differs from the $C_T$ value observed by an identical level of the nucleic acid in a lysate.

In various embodiments, the use of a normalizer control may control for a variable in a proximity detection assay. Certain exemplary variables in proximity detection assays include, but are not limited to, nucleic acid degradation, analyte degradation, the extent to which analyte epitope structure has been maintained, the efficiency with which a proximity detection probe binds to an analyte, the efficiency of a ligation reaction, and the efficiency of a real-time PCR reaction.

In various embodiments, an analyte normalizer control is detected using a proximity detection assay. Certain exemplary proximity detection assays are described herein. In certain embodiments, an analyte normalizer control is detected using the same method (using appropriate proximity detection probes) and in the same vessel as a target analyte. In certain embodiments, an analyte normalizer control is detected using the same method (using appropriate proximity detection probes) but in a different vessel as a target analyte.

In various embodiments, nucleic acid normalizer controls and/or proximity detection probes used to detect analyte normalizer controls are detected by direct detection methods or by detection methods involving an amplification step. Certain exemplary methods of detecting nucleic acids and/or proximity detection probes are described herein. In certain embodiments, different labels are used to detect nucleic acid normalizer controls, target nucleic acids, proximity detection probes used to detect analyte normalizer controls, and/or proximity detection probes used to detect target analytes.

In various embodiments where a nucleic acid normalizer control is an RNA, the nucleic acid normalizer control is subjected to pretreatment to convert it to a form that can be detected using the same method used to detect a proximity detection probe, a target nucleic acid, and/or a second nucleic acid normalizer control.

In certain embodiments, a nucleic acid normalizer control and/or a proximity detection probe used to detect an analyte normalizer control is detected using real-time PCR. In certain embodiments, a nucleic acid normalizer control and/or proximity detection probe used to detect an analyte normalizer control is detected using a combination of PCR and ligation. For example, in certain embodiments a nucleic acid normalizer control and/or proximity detection probe used to detect an analyte normalizer control is detected by first amplifying by PCR, and then applying a ligation inquiry. Certain exemplary such methods are known in the art, and are described, e.g., in Chen et al., "A homogeneous, ligase-mediated DNA diagnostic test," *Genome Res.* 8(5):549-56 (1998).

In certain embodiments, a nucleic acid normalizer control is detected using a method that involves first performing a ligation reaction, followed by PCR amplification. Certain exemplary such methods are known in the art and are described, e.g., in U.S. Pat. No. 4,797,470. For example, in certain embodiments a nucleic acid normalizer control is capable of hybridizing to at least two oligonucleotides. In certain embodiments, the at least two oligonucleotides are capable of being joined by ligation. In certain embodiments, the ligatable ends of each of the oligonucleotides are brought together by the nucleic acid normalizer control. In certain embodiments, two oligonucleotides hybridize to the ligation template such that the 3' end of a first oligonucleotide is adjacent to the 5' end of a second oligonucleotide. In certain embodiments, the ligatable ends of each of the oligonucleotides are joined by ligation. In certain embodiments, the ligation is mediated by a ligase enzyme. Detection of a nucleic acid normalizer control by a method that involves ligation may, in certain embodiments, control for the efficiency of a ligation reaction step in a proximity detection assay.

Certain Exemplary Blocking Agents

In certain embodiments, a proximity detection assay is performed in the presence of at least one blocking agent. In various embodiments, a proximity detection assay is performed in the presence of an analyte blocking agent and/or a nucleic acid blocking agent. In certain embodiments, an analyte blocking agent is a protein. In certain embodiments, a protein blocking agent is a gelatin. In certain embodiments, a nucleic acid blocking agent is a predominantly single-stranded nucleic acid. In certain embodiments, a nucleic acid blocking agent is a predominantly double-stranded nucleic acid.

In certain embodiments, at least one blocking agent is added to a multifunctional lysis buffer. In certain embodiments, at least one blocking agent is added to a lysate. In certain embodiments, at least one blocking agent is added to a lysate prior to or simultaneous with the addition of one or more proximity detection probes. In certain embodiments, at least one blocking agent is added to a lysate prior to detection of hybridized and/or ligated nucleotide moieties and/or target nucleic acid. In certain embodiments, at least one analyte blocking agent and at least one nucleic acid blocking agent are added. In various embodiments, when more than one blocking agent is added, they may be added at the same or different times.

Figure 20:
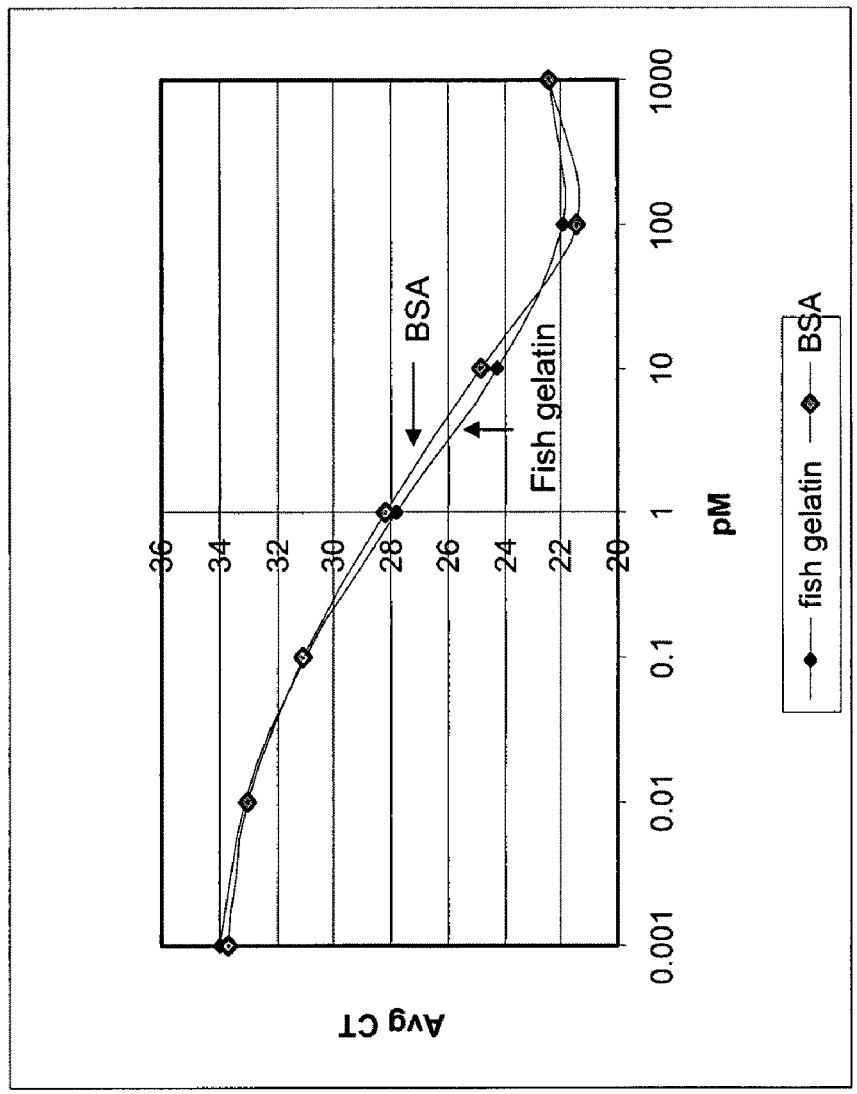
FIG. 20 shows exemplary data from proximity ligation assays (PLA) carried out to detect various concentrations of VEGF in buffer containing either 0.1% fish gelatin or 1% BSA. Exemplary data is plotted as average threshold cycle (avg CT) versus pM VEGF.

FIG. 20 shows exemplary results of a proximity ligation assay to detect VEGF, carried out in the presence of certain analyte blocking agents, 0.1% cold fish gelatin and 1% BSA. In those exemplary results, the proximity ligation reaction performs equally well in 0.1% cold fish gelatin and 1% BSA.

Figure 21:
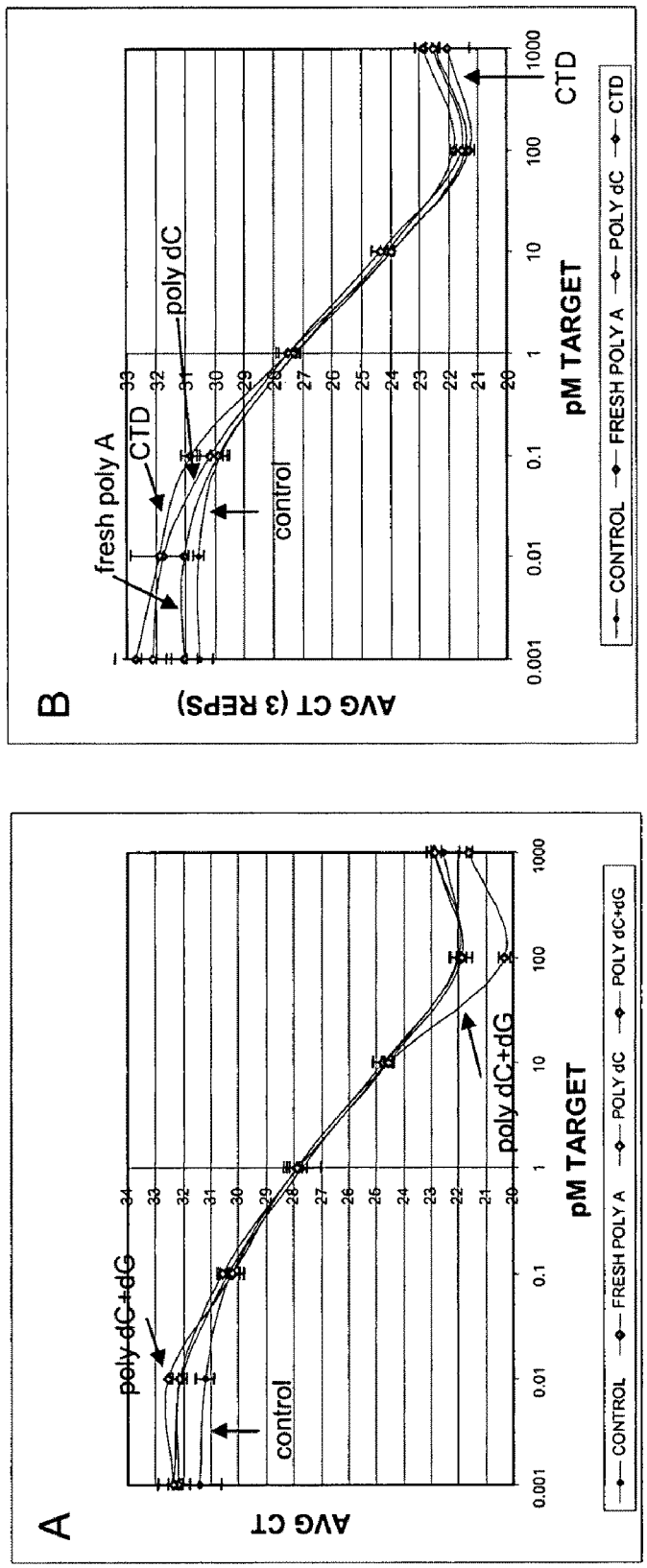
FIG. 21 shows exemplary data from proximity ligation assays (PLA) carried out to detect various concentrations of VEGF in buffer containing 0.1% fish gelatin and various nucleic acid blocking agents. Panel A shows exemplary data from the proximity ligation assays containing polyA stored at 4° C. for at least 2 weeks (control), polyA, polydc, and polydC+polydG. Panel B shows exemplary data from the proximity ligation assays containing polyA stored at 4° C. for at least 2 weeks (control), polyA, polydc, and sheared calf thymus DNA (CFD). Exemplary data is plotted as average threshold cylce (avg CT) versus pM VEGF.

FIG. 21 shows exemplary results of a proximity ligation assay to detect VEGF, carried out in the presence of certain nucleic acid blocking agents, polyA, polydc, polydG+polydC, and sheared calf thymus DNA ("CFD"). The controls in FIG. 21 are carried out in the presence of polyA stored at 4° C. for at least 2 weeks. In those exemplary results, the proximity ligation assays carried out in the presence of double-stranded nucleic acid blocking agents (polydG+polydC and sheared calf thymus DNA) showed a greater range of detection than the proximity ligation assays carried out in the presence of single-stranded nucleic acid blocking agents (polyA, and polydc).

Certain Exemplary Ligation Reaction Termination

In certain embodiments, a ligation reaction in a proximity ligation assay is terminated prior to detection of the ligated product. In certain embodiments, a ligation reaction is terminated prior to storing the proximity ligation assay. The proximity ligation assay may be stored before or after detection of the ligated product. In certain embodiments, termination of the ligation reaction reduces the amount of additional ligated products that may accumulate over time, for example, during storage of a proximity ligation assay.

In certain embodiments, the ligation reaction is terminated by treatment with a protease. Certain exemplary proteases are described herein. In certain embodiments, a ligation reaction is terminated by altering the splint oligonucleotide. In certain embodiments, a splint oligonucleotide used in a proximity detection assay comprises deoxy-uracil (dU) in place of deoxy-thymine (dT). In certain embodiments, the dU-containing splint oligonucleotide is altered by adding uracil-DNA glycosylase (UNG) to the proximity detection assay after the ligation step. In certain embodiments, altering the splint oligonucleotide reduces unwanted primer extension products that may form during detection of ligated products.

Figure 22:
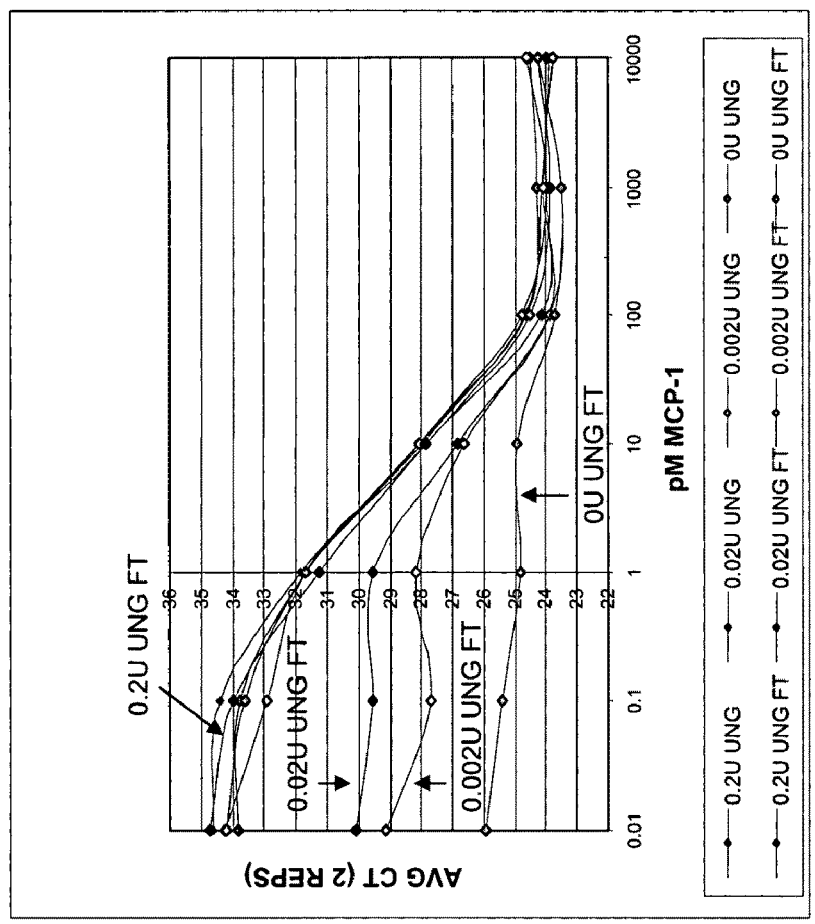
FIG. 22 shows exemplary data from proximity ligation assays carried out to detect various concentrations of MCP-1 using a splint oligonucleotide that contains deoxy-uracil (dU). The assays were carried out with and without treatment with uracil-DNA glycosylase, and with (dashed lines) and without (solid lines) a freeze-thaw cycle prior to detection of the ligation products. Exemplary data is plotted as average threshold cycle (avg CT) versus pM MCP-1.

FIG. 22 shows exemplary results of proximity ligation assays to detect MCP-1 using a dU-containing splint oligonucleotide. The assays were carried out with and without UNG treatment after the ligation reaction, and with and without a freeze-thaw cycle prior to detection of the ligation products. Exemplary treatment with 0 U, 0.002 U, 0.02 U, and 0.2 U of UNG are shown. UNG treatment is carried out at 37° C. for 15 minutes, followed by 95° C. for 3 minutes in that exemplary experiment. Additionally, qPCR is carried out to detect the ligation products in that exemplary experiment immediately after UNG treatment (solid lines) and 24 hours after UNG treatment with one cycle of freeze-thawing (dashed lines). The exemplary data shows that the inclusion of an UNG incubation step, in certain embodiments, reduces the accumulation of ligation products over time.

Certain Exemplary Detection of Proximity Detection Probes and Target Nucleic Acids In various embodiments, the hybridized and/or ligated oligonucleotide moieties of the proximity detection probes and the target nucleic acid may be detected, in various embodiments, separately and/or simultaneously. In certain embodiments, the hybridized and/or ligated oligonucleotide moieties of the proximity detection probes and the target nucleic acid are detected in the same vessel, either simultaneously or at different times. In certain embodiments, e.g., when the target nucleic acid is an RNA, the target nucleic acid is subjected to pretreatment to convert it to a form that can be detected using the same method as the hybridized and/or ligated oligonucleotide moieties of the proximity detection probes. Such pretreatments include, but are not limited to, reverse transcription.

In certain embodiments, the hybridized and/or ligated oligonucleotide moieties of the proximity detection probes are subjected to a pretreatment to convert them to a form that can be detected using the same method for detecting the target nucleic acid. Such pretreatments include, but are not limited to, ligation and primer extension reactions. In certain embodiments, when detection of the hybridized and/or ligated oligonucleotide moieties involves amplification, the pretreatment primer extension reaction may not be necessary, because the amplification conditions will allow the primer extension reaction to occur prior to, or simultaneously with, amplification.

In certain embodiments, the lysate is split or divided and the target nucleic acid and the hybridized and/or ligated oligonucleotide moieties of the proximity detection probes are detected in separate vessels, using the same or different methods. In certain embodiments, the lysate is divided after the proximity detection probes have been hybridized and/or ligated. In certain embodiments, the lysate is divided after all of the processes leading up to detection have been carried out. For example, in certain embodiments, the lysate is divided solely to facilitate separate detection of the proximity detection probe sets and the target nucleic acids, for example, so the same detector probes may be used in each detection method. In various embodiments, the lysate may be divided after lysis, after binding the proximity detection probes, after hybridization and/or ligation of the proximity detection probes, or after protease treatment.

In certain embodiments where the target nucleic acid is an RNA, the target nucleic acid is subjected to reverse transcription either before or during the selected detection method. The DNA copy of the target nucleic acid is also referred to as the target nucleic acid (although the RNA copy may be referred to as the target RNA nucleic acid and the DNA copy may be referred to as the target DNA nucleic acid). In various embodiments, after the target nucleic acid RNA has been reverse transcribed into a target nucleic acid DNA, the target nucleic acid DNA may be detected by the same method as the hybridized and/or ligated oligonucleotide moieties of the proximity detection probes. In certain embodiments, the target nucleic acid DNA and the hybridized and/or ligated oligonucleotide moieties of the proximity detection probes are detected simultaneously in the same vessel and by the same detection method.

In certain embodiments, multiple hybridized and/or ligated oligonucleotide moieties of proximity detection probes and/or multiple target nucleic acids are detected simultaneously in the same vessel. In certain embodiments, different labels are used to identify the different proximity detection probe sets and the different target nucleic acids. For example, in certain embodiments, if five target analytes and five target nucleic acids are being detected in a biological sample, and a single detection reaction is used to detect the hybridized and/or ligated oligonucleotide moieties of the five different proximity detection probe sets and the five different target nucleic acids, ten different labels may be used to separately identify the different products. In various embodiments, such labels may be in the form of detector probes, discussed herein, or any other label known in the art that is suitable for use in the detection methods. One skilled in the art can select an appropriate label or labels, according to various embodiments.

In certain embodiments, the hybridized and/or ligated oligonucleotide moieties of the proximity detection probes and/or the target nucleic acid are detected using real-time PCR. Exemplary methods of performing real-time PCR include, but are not limited to, 5' nuclease real-time PCR, and multiplexed versions thereof. Certain exemplary methods of 5' nuclease real-time PCR are known in the art and are described, e.g., in Livak, "SNP genotyping by the 5'-nuclease reaction," *Methods Mol Biol.* 212:129-47 (2003); Lee et al., "Seven-color, homogeneous detection of six PCR products," *Biotechniques* 27(2):342-9 (1999); Livak, "Allelic discrimination using fluorogenic probes and the 5' nuclease assay," *Genet Anal.* 14(5-6):143-9 (1999); Heid et al., "Real time quantitative PCR," *Genome Res.* 6(10):986-94 (1996); and Lee et al., "Allelic discrimination by nick-translation PCR with fluorogenic probes," *Nucleic Acids Res.* 11;21(16):3761-6 (1993). Exemplary quantitative PCR is described, e.g., in *A-Z Quantitative PCR*, Bustin, S., Ed., IUL Biotechnology Series (2004). Certain exemplary methods of real-time PCR are also described, e.g., in Watson et al., *Int J Toxicol.* 2005 May-June; 24(3):139-45, and U.S. Pat. Nos. 6,890,718; 6,773,817; and 6,258,569. In certain embodiments, a target nucleic acid is detected using TaqMan One-step qRT-PCR (Applied Biosystems).

In various embodiments, passive reference dyes may be used in quantitative PCR methods. Certain exemplary passive reference dyes are described, e.g., in U.S. Pat. No. 5,736,333. In various embodiments, external controls may be used in quantitative PCR methods. Certain exemplary quantitative controls are described, e.g., in U.S. Pat. No. 6,890,718.

In certain embodiments, the hybridized and/or ligated oligonucleotide moieties of the proximity detection probes and/or the target nucleic acid are detected using a combination of PCR and ligation. As a non-limiting example, hybridized and/or ligated oligonucleotide moieties of the proximity detection probes may be detected by first amplifying by PCR, and then applying a ligation inquiry. Certain exemplary such methods are known in the art, and are described, e.g., in Chen et al., "A homogeneous, ligase-mediated DNA diagnostic test," *Genome Res.* 8(5):549-56 (1998). As a further non-limiting example, hybridized and/or ligated oligonucleotide moieties of the proximity detection probes may be detected by first performing a ligation reaction, followed by PCR amplification. Certain exemplary such methods are known in the art and are described, e.g., in U.S. Pat. No. 4,797,470.

In various embodiments, the ligation assay may comprise a flap endonuclease, e.g., as described in U.S. Pat. No. 6,511,810.

In certain embodiments, the hybridized and/or ligated oligonucleotide moieties of the proximity detection probes and/or the target nucleic acid are amplified in a first "pre-amplification reaction" (described, e.g., in PCT Publication No. WO2004/051218), and then decoded in a second amplification reaction. Certain exemplary such methods are known in the art and are described, e.g., in U.S. Pat. No. 6,605,451; U.S. patent application Ser. No. 11/090,468 to Lao et al., and U.S. patent application Ser. No. 11/090,830 to Andersen et al.

Certain exemplary methods of detecting the hybridized and/or ligated oligonucleotide moieties of the proximity detection probes and/or the target nucleic acid are also described, e.g., in U.S. Pat. No. 6,511,809 B2; U.S. Publication No. US 2002/0064779 A1; and PCT Publication No. WO 2005/123963. Certain exemplary multiplex detection methods are described, e.g., in U.S. patent application Ser. No. 11/372,242 to Bodeau et al.

In various embodiments, a detector probe is used to facilitate detection of the hybridized and/or ligated oligonucleotide moieties of the proximity detection probes and/or the target nucleic acid and/or an amplification product. Certain exemplary detector probes are discussed herein. In various embodiments, one skilled in the art can select one or more suitable detector probes according to the intended application.

Exemplary Kits

In various embodiments, kits comprising at least one component for carrying out the methods are provided. In various embodiments, a kit comprises at least one multifunctional lysis buffer. In various embodiments, a kit comprises at least one proximity detection probe set. In various embodiments, a kit comprises at least one protease. In various embodiments, a kit comprises at least one ligase. In various embodiments, a kit comprises at least one normalizer control.

In various embodiments, a kit comprises at least one component for detecting a proximity detection probe set and/or a target nucleic acid. In various embodiments, a kit comprises at least one component for detecting a normalizer control. Exemplary components include, but are not limited to, detector probes, primers, polymerases, and reverse transcriptases.

EXAMPLES

Example 1

Quantitative Detection of Protein and mRNA in Cell Lysates

Raji human B-cell lymphoma cells were pelleted by centrifugation at 1000×g for 5 minutes. The cells were resuspended at a concentration of 50,000 cells per µl of PBS. An equal volume of 2× Buffer N (2× Buffer N is 0.2% NDSB-201, 50 mM Tris-HCl pH 8.0, and 1 mM EDTA pH 8.0) was added to the suspension and mixed thoroughly by vortexing for 5 seconds.

Proximity Ligation Assay

Five target analytes were selected for detection by proximity ligation assay. The target analytes were ADAM9 (ADAM metallopeptidase domain 9; http://www.genecards.org/cgi-bin/carddisp.pl?gene=ADAM9&search=ADAM9); CCL5 (chemokine (C—C motif) ligand 5; http://www.genecards.org/cgi-bin/carddisp.pl?gene=CCL5&search=ccl5); CSTB (Cystatin B; http://www.genecards.org/cgi-bin/carddisp.pl?gene=CSTB&search=cystatin+B); SMAD4 (Mothers against DPP homolog 4; http://www.genecards.org/cgi-bin/carddisp.pl?gene=SMAD4&search=smad4); and RUNX1 (Runt-related transcription factor 1; http://www.genecards.org/cgi-bin/carddisp.pl?gene=RUNX1&search=runx1). In this experiment, the proximity ligation assays for each target analyte were carried out separately.

The proximity detection probes were provided by Simon Fredriksson. Exemplary proximity detection probes and methods of designing proximity detection probes are described in PCT Publication No. WO 2005/123963. For each target analyte, two oligonucleotides were synthesized, the first with a 5'-conjugated streptavidin, and the second with a 3'-conjugated streptavidin. 5 µl of a 200 nM stock of the first streptavidin-conjugated oligonucleotides was mixed with 5 µl of a 200 nM stock of biotinylated polyclonal antibody to the selected target analyte (all biotinylated polyclonal antibodies were from R&D Systems) in Buffer C (1×PBS pH 7.4, 0.1% BSA, 5 nM EDTA). Similarly, 5 µl of a 200 nM stock of the second streptavidin-conjugated oligonucleotides was mixed with 5 µl of a 200 nM stock of the biotinylated polyclonal antibody to the selected target analyte in Buffer C. The mixtures were incubated for 1 hour at room temperature. Each proximity detection probe was diluted to 1 nM in Buffer D (1×PBS pH 7.4, 1% BSA, 1 mM biotin, and 16 µg/ml polyA) by adding 99 µl Buffer D to 1 µl of the proximity detection probe. This resulted in first and second proximity detection probes (i.e., a proximity detection probe set) for each of the five target analytes.

To form five separate solutions, each with one of the five different proximity detection probe sets, the first and second proximity detection probes of a probe set were combined in Buffer D at a concentration of 100 pM for each proximity detection probe. Three concentrations of cell lysate were prepared by dilution with Buffer D, having an equivalent of 5000, 500, or 50 cells per µl. A phosphatase inhibitor cocktail (100×HALT Phosphatase Inhibitor Cocktail, Pierce Catalog #78420) was added to the cell lysate dilutions to a concentration of 1× to protect the 5' phosphate of the second proximity detection probe. 1 µl of the cell lysate in Buffer N was mixed with 1 µl of the proximity detection probe pair solution and incubated for 1 hour at 37° C. The concentration of each proximity detection probe in the probe binding mixture was 50 pM.

For probe ligation, a splint oligonucleotide(s) were provided by Simon Fredriksson. Exemplary splint oligonucleotides and methods of designing splint oligonucleotides are described in PCT Publication No. WO 2005/123963. Each splint oligonucleotide was capable of hybridizing to a portion of each of the oligonucleotide moieties of the proximity detection probe set such that the free 3' end of the first oligonucleotide moiety in the proximity detection probe set is adjacent to the free 5' end of the second oligonucleotide moiety in the proximity detection probe set. Each splint oligonucleotide was asymmetric (see, e.g., PCT Publication No. WO 2005/123963). 120 µl of ligation solution (1×PCR II buffer (Applied Biosystems), 100 nM splint oligonucleotide, 1.5 mM $MgCl_2$, 0.3 mM NAD, 10 mM DTT, and 2.5 units Ampligase (Epicentre)) was added to the probe binding mixture. The equivalent concentration of Raji cells in the three ligation mixtures for each proximity detection probe set was about 41.7 cells/µl, 4.17 cells/µl, and 0.417 cells/µl. The ligation mixture was incubated at 30° C. for 10 minutes. 20 µl of the ligation mixtures containing about 41.7 cells/µl and 4.17 cells/µl were removed and saved for mRNA detection (described below).

The ligated proximity detection probe set was detected using real-time PCR as follows. 10 µl of the ligation mixture was mixed with 10 µl of 2× Power SYBR Green PCR Master Mix (Applied Biosystems; catalog no. 4367218) and 0.04 µl each of forward and reverse primers designed to amplify the ligated oligonucleotide moieties of the proximity detection probe pairs, but not the unligated proximity detection probes (final primer concentration was 400 nM for each primer). Forward and reverse primers were provided by Simon Fredriksson. Exemplary forward and reverse primer sequences are described in PCT Publication No. WO 2005/123963. Real-time PCR was carried out according to the Power SYBR Green PCR Master Mix protocol (Applied Biosystems; catalog no. 4310251).

mRNA Detection

A 20 µl sample of the ligation mixture was treated with 5 µl of *streptomyces griseus* protease (Fluka catalog no. 81748; 6.34 U/mg, concentration 2.5 U/µl) for 60 minutes at 37° C. The mixture was then heated to 75° C. for 10 minutes to reduce or eliminate protease activity. The protease-treated ligation mixture is referred to as the "mRNA sample." The equivalent concentration of Raji cells in the two mRNA samples for each proximity detection probe set was about 33.3 cells/µl and 3.33 cells/µl.

The 25 µl mRNA sample was diluted about 1:5 by adding 100 µl water and 5 µl of 50 µg/µl BSA (Ambion; catalog no. 2616). The final concentration of BSA in the diluted mRNA sample was therefore about 2 µg/µl, and the equivalent concentration of Raji cells in the two diluted mRNA samples for each proximity detection probe set was about 6.6 cells/µl and 0.66 cells/µl. 5 µl of the diluted mRNA sample was used in a 25 µl TaqMan One-step qRT-PCR reaction. The equivalent total number of Raji cells in the RT-PCR reactions for each proximity detection probe set was about 33 cells and 3.3 cells, which equals about 0.5 ng total RNA and 0.05 ng total RNA, respectively, assuming an RNA concentration of about 15 µg/cell. TaqMan gene expression assay primers and probe (Applied Biosystems; catalog nos: SMAD4: Hs00232068_m1; CCL5: Hs00174575_m1; CSTB: Hs00164368_m1; ADAM9: Hs00177638_m1; RUNX1: Hs00234079_m1) were used at 1× concentration and the one-step RT-PCR reaction was carried out using the Applied Biosystems TaqMan One-step RT-PCR Mastermix Reagents kit according to the manufacturer's protocol (Applied Biosystems; kit catalog no. 4309169; protocol catalog no. 4310299). Detection of 18S RNA in the ligation mixture was used as a control (using 18S RNA Control Reagent, Applied Biosystems, catalog no. 4308329). Finally, 100 ng RNA purified from Raji cells was used as a positive control for each selected target. Each reaction was done in triplicate, except the positive controls, which were done in single wells. The five selected target analytes were all detected using FAM, while the 18S was detected using VIC.

The results of the proximity ligation assays and the mRNA detection assays in that experiment were as follows. FIG. 1 shows the average threshold cycle (Ct) for each target analyte at the three Raji cell lysate concentrations tested. That data demonstrates that this proximity ligation assay experiment successfully detected CSTB in a dose-dependent manner.

Figure 2:
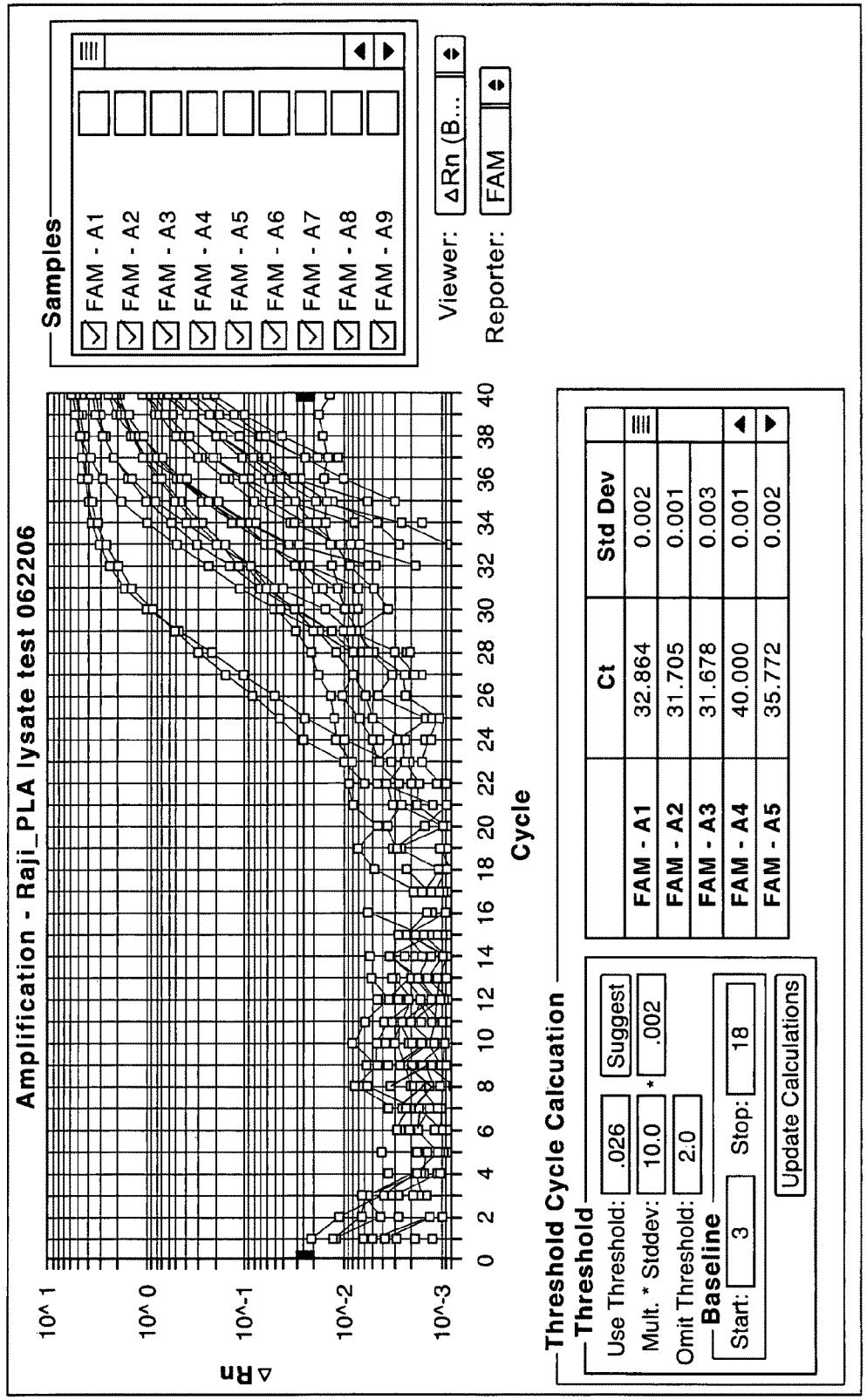
FIG. 2 shows a plot of the relative increase in fluorescence (ΔRn) versus cycle number for the TaqMan One-step qRT-PCR reactions described in Example 1. Only the FAM layer is shown in FIG. 2.

FIG. 2 shows the relative increase in fluorescence (ΔRn) versus cycle for each of the TaqMan One-step qRT-PCR reactions used to detect the target mRNA, as discussed above. Only the FAM layer is detected in FIG. 2, so the 18S reactions, which used VIC, are not detectable. Each reaction, except the positive controls, was done in triplicate. That data shows that nearly all of the TaqMan One-step qRT-PCR reactions produced detectable amplification products. The steep relative increase in fluorescence suggests relatively robust amplification was achieved for each target mRNA.

Figure 3:
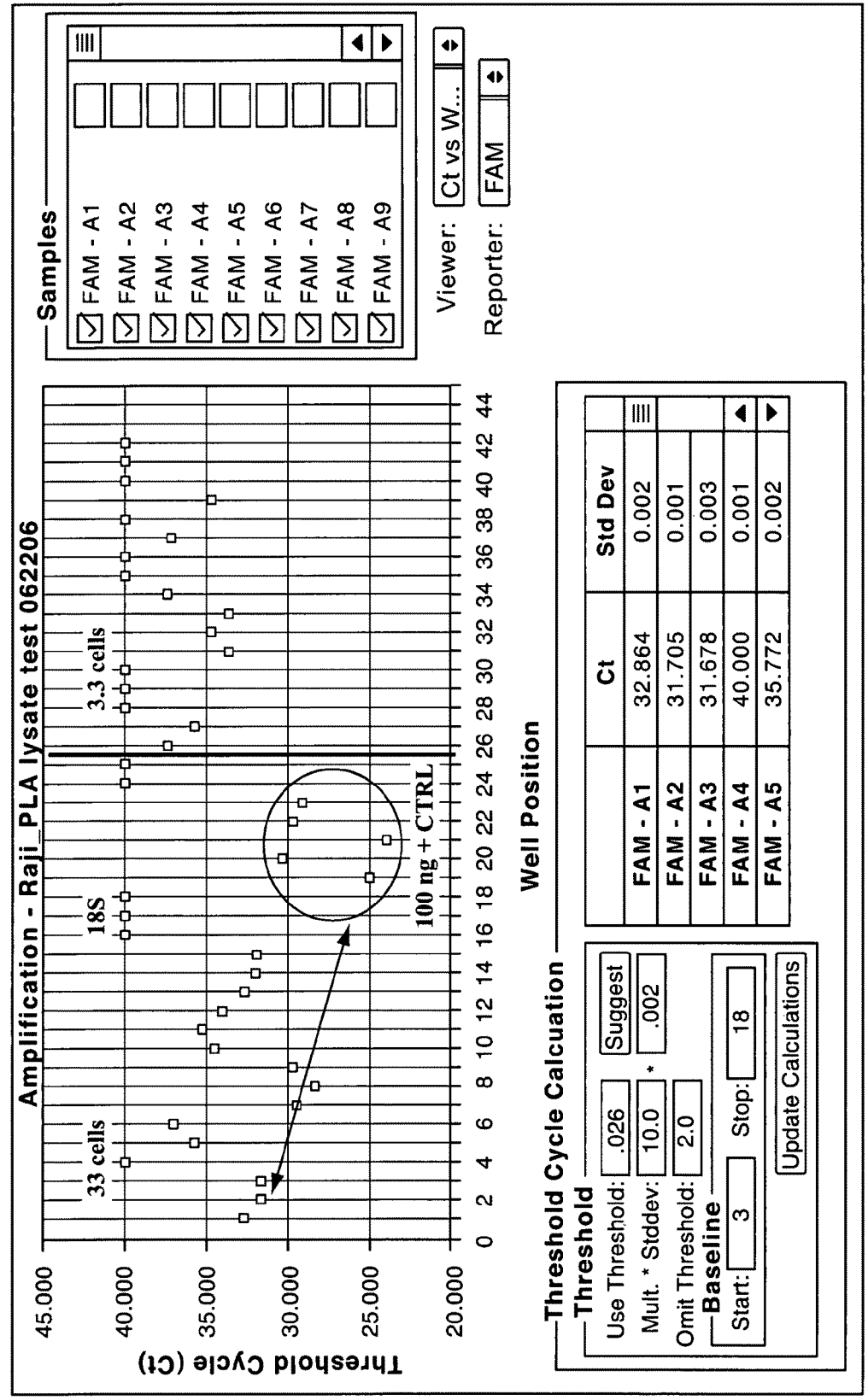
FIG. 3 shows a plot of the threshold cycle number versus the plate location (i.e., TaqMan One-step qRT-PCR reaction) for the experiment described in Example 1. Only the FAM layer is shown in FIG. 3.

FIG. 3 shows a plot of the threshold cycle (Ct) for each of the TaqMan One-step qRT-PCR reactions, by well position in the 96-well plate in which the reactions were performed. Only the FAM layer is detected in FIG. 3, so the 18S reactions, which used VIC, are not detectable. The well positions of the reactions were as follows. Wells A1-A12 (1-12 on FIG. 3) contained triplicate reactions using the higher Raji cell equivalent concentration (33 cells per reaction) for four of the five target mRNAs (ADAM9 in wells A1-A3, CCL5 in wells A4-A6, CSTB in wells A7-A9, SMAD4 in wells A10-A12). Wells B1-B6 (13-18 on FIG. 3) contained triplicate reactions using the highest Raji cell equivalent concentration (33 cells per reaction) for RUNX1 (wells B1-B3) and the control RNA, 18S (wells B4-B6). Wells B7-B12 (19-24 on FIG. 3) contained the positive control reactions, using 100 ng of purified RNA from Raji cells to detect each selected target (ADAM9, CCL5, CSTB, SMAD4, RUNX1 in wells B7-B11, respectively) and 18S RNA (well B12). Wells $C_1$-$C_{12}$ (25-36 on FIG. 3) contained triplicate reactions using the lower Raji cell equivalent concentration (3.3 cells per reaction) for four of the five target mRNAs (ADAM9 in wells $C_1$-$C_3$, CCL5 in wells $C_4$-$C_6$, CSTB in wells $C_7$-$C_9$, SMAD4 in wells $C_{10}$-$C_{12}$). Wells D1-D6 (13-18 on FIG. 3) contained triplicate reactions using the lower Raji cell equivalent concentration (3.3 cells per reaction) for RUNX1 (wells D1-D3) and the control RNA, 18S (wells D4-D6). Those data show that the mRNA for all of the selected targets were detected in TaqMan One-step qRT-PCR reactions using 33 cells per reaction.

Assuming that 33 cells per reaction is equivalent to about 0.5 ng RNA per reaction, the positive control reactions, which used 100 ng purified Raji RNA, contained about 200× more RNA. With 200× more RNA, the difference in the threshold cycle (ΔCt) is expected to be about 7.6, which is roughly what was observed (compare wells 1-3 with well 19, wells 4-6 with well 20, wells 7-9 with well 21, wells 10-12 with well 22, wells 13-15 with well 23). The measured average ΔCt was 6.99 for ADAM9, 6.00 for CCL5, 5.21 for CSTB, 4.97 for SMAD4, and 3.03 for RUNX1.

Figure 4:
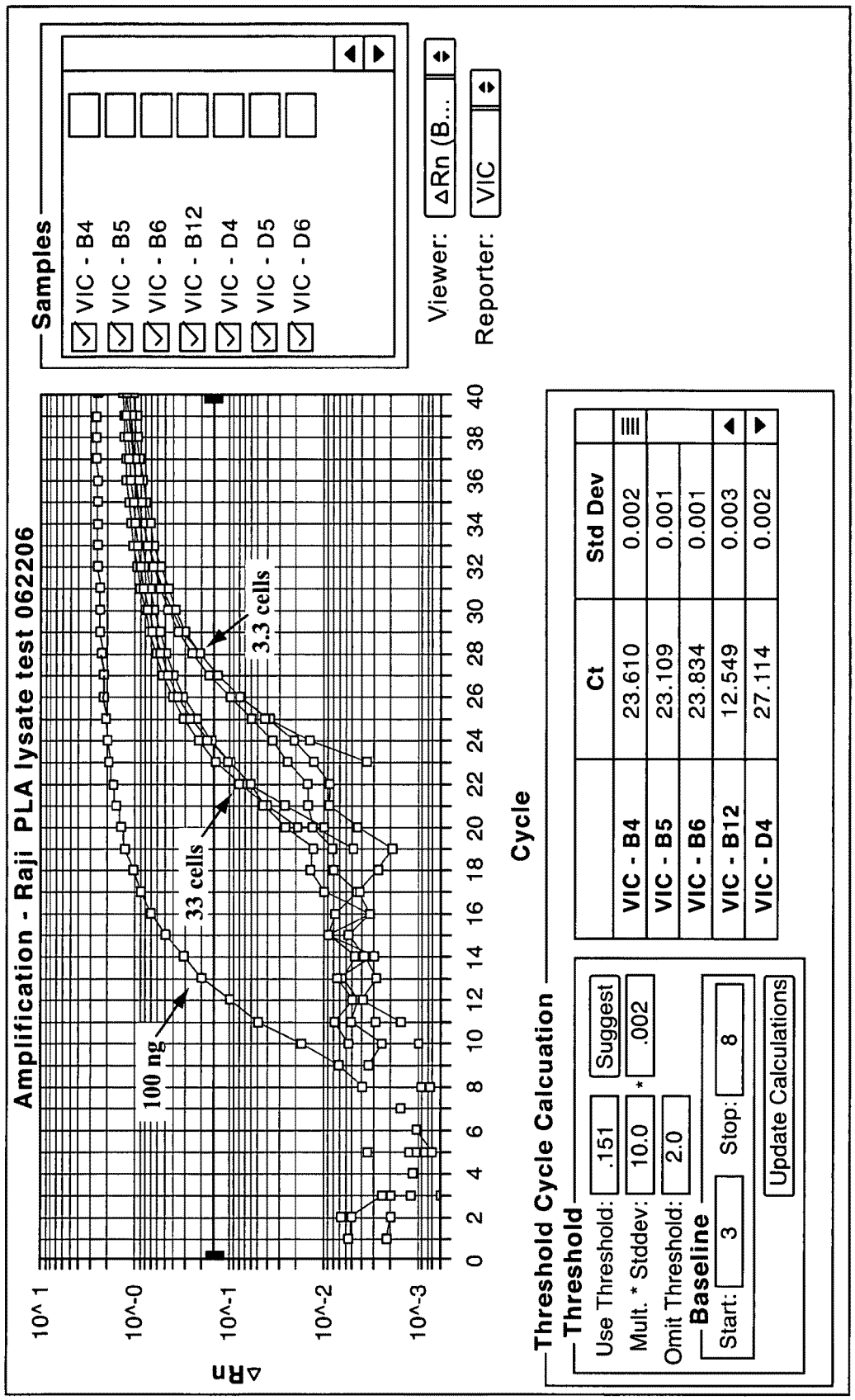
FIG. 4 shows a plot of the relative increase in fluorescence (ΔRn) versus cycle number for the TaqMan One-step qRT-PCR reactions described in Example 1. Only the VIC layer is shown in FIG. 4.

FIG. 4 shows the relative increase in fluorescence (ΔRn) versus cycle for each of the TaqMan One-step qRT-PCR reactions used to detect the 18S RNA. Only the VIC layer is detected in FIG. 4, so the target mRNA reactions, which used FAM, are not detectable. Each reaction, except the positive controls, was done in triplicate. That data shows that all of the TaqMan One-step qRT-PCR reactions to detect 18S RNA produced detectable amplification products. The steep relative increase in fluorescence suggests that robust amplification was achieved for the 18S RNA in all reactions.

Figure 5:
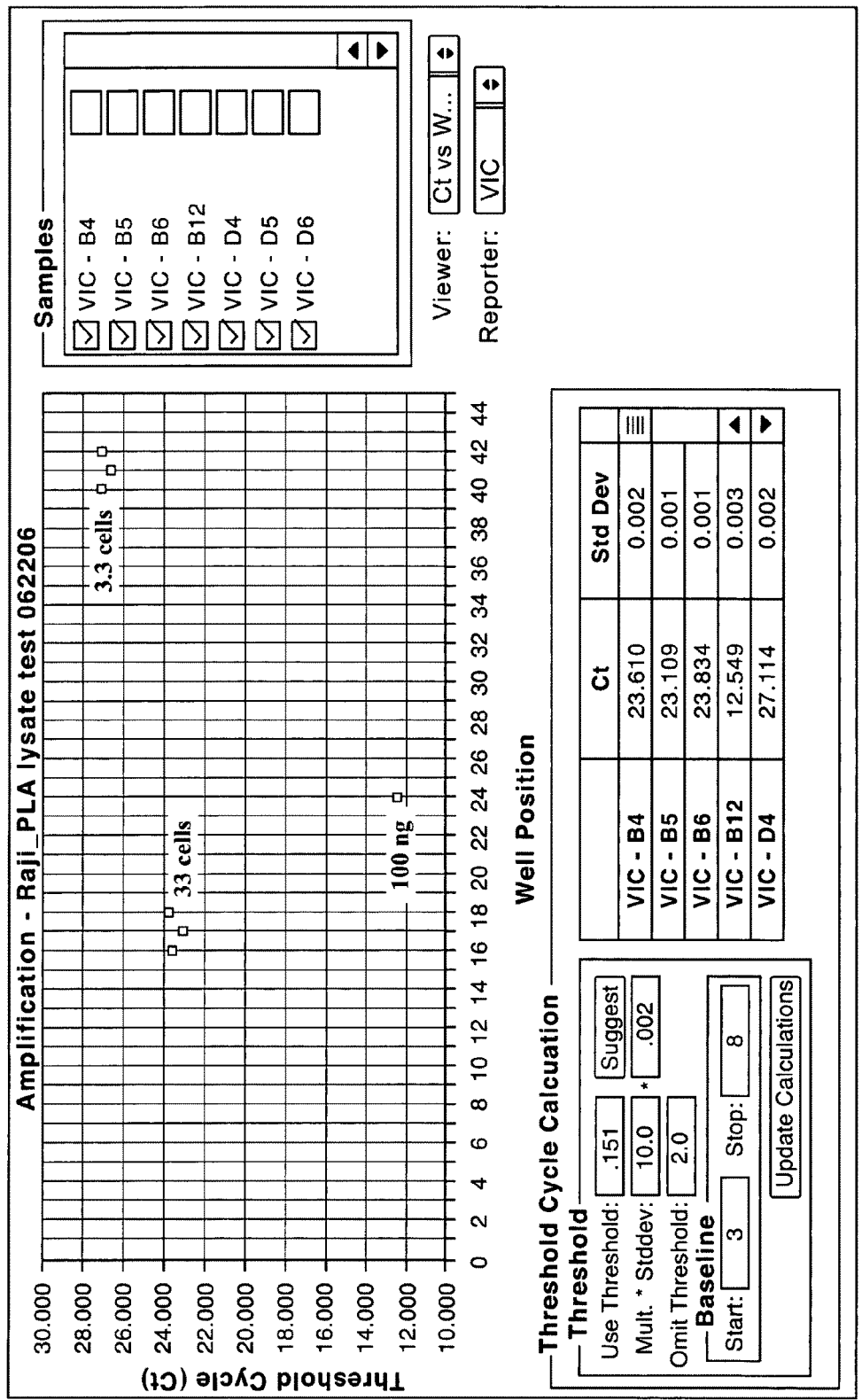
FIG. 5 shows a plot of the threshold cycle number versus the plate location (i.e., TaqMan One-step qRT-PCR reaction) for the experiment described in Example 1. Only the VIC layer is shown in FIG. 5.

FIG. 5 shows a plot of the threshold cycle (Ct) for each of the TaqMan One-step qRT-PCR reactions, by well position in the 96-well plate in which the reactions were performed. Only the VIC layer is detected in FIG. 3, so only the 18S reactions are detectable. The well positions of the reactions are as discussed above for FIG. 3. Those data showed that the 18S RNA was detectable in each reaction.

Example 2 mRNA Detection with and without RT and with and without Protease Treatment

An mRNA detection experiment was conducted to measure 18S RNA levels in reactions with and without reverse transcriptase (RT). Reactions were also carried out with and without protease treatment. By carrying out the reactions with and without RT, the ΔCt between reactions containing RNA and genomic DNA and reactions containing only genomic DNA can be determined.

In this experiment, Raji cells were lysed at a final concentration of 5000 cells/μl in three different lysis buffers. The first buffer, Buffer Na, contained 10% NDSB-201, 50 mM Tris 8.0, and 1 mM EDTA; the second buffer, Buffer Nb, contained 1% NDSB-201, 50 mM Tris 8.0, and 1 mM EDTA; and the third buffer, Buffer Nc, contained 0.1% NDSB-201, 50 mM Tris 8.0, and 1 mM EDTA. Half of each Raji cell lysate was treated with *streptomyces griseus* protease (2.5 U/μl) at 37° C. for 30 minutes, and then heat treated at 75° C. for 5 minutes. The other half of the samples were incubated at 37° C. for 30 minutes, and then heat treated at 75° C. for 5 minutes, but did not receive protease. The protease treated samples became viscous while the untreated samples did not.

Figure 6:
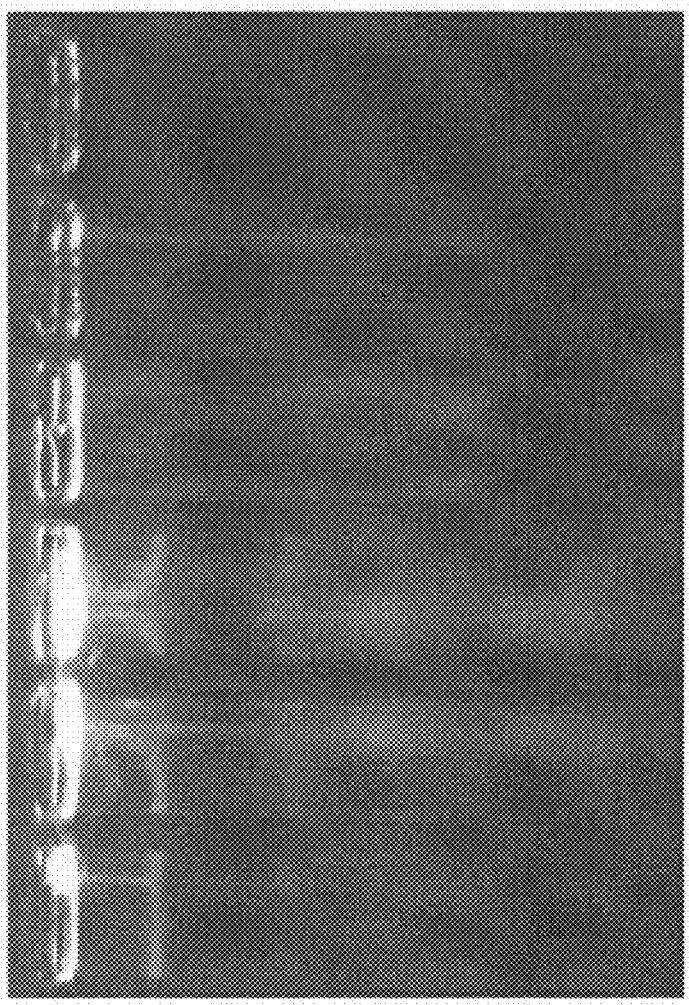
FIG. 6 shows agarose gel electrophoresis of lysates prepared in Buffer Na, Buffer Nb, and Buffer Nc, with and without protease, as described in Example 2.

FIG. 6 shows agarose gel electrophoresis of 10 μl of each lysate. That gel shows that the protease-treated samples released RNA and genomic DNA, while the untreated samples did not.

The three Raji cell lysates (in Buffer Na, Buffer Nb, and Buffer Nc) were then diluted in 50 mM Tris pH 8.0, 1 mM EDTA as necessary to normalize to a concentration of 0.1% NDSB-201. As a result, the diluted Buffer Na lysate contained 50 cells per μl, the diluted Buffer Nb lysate contained 500 cells per μl, and the Buffer Nc lysate remained at 5000 cells per μl. 5 μl of lysate was used in each 25 μl TaqMan One-step qRTPCR reaction, to detect 18S RNA. Each lysate (each cell concentration, protease treated and untreated) was tested with and without RT, in triplicate. The reactions were analyzed using an ABI PRISM 7700 system.

Figure 7:
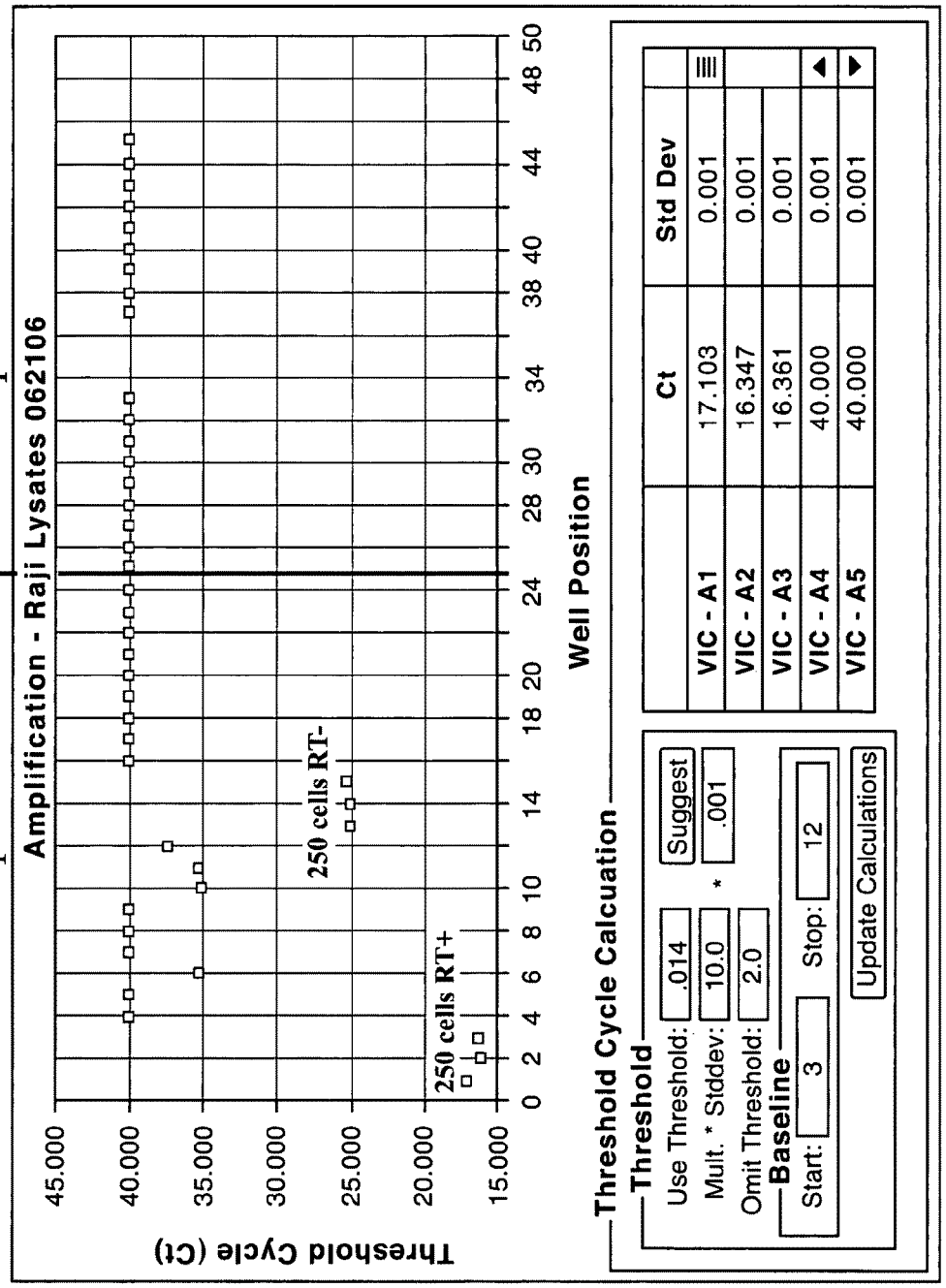
FIG. 7 shows a plot of the threshold cycle number versus the plate location (i.e., TaqMan One-step qRT-PCR reaction) for the experiment described in Example 2.

FIG. 7 shows the results of that experiment. The well positions of the reactions were as follows. Wells A1-A12 (1-12 in FIG. 7) contained reactions with RT, using protease-treated lysates: 250 cells/reaction (wells A1-A3), 2500 cells/reaction (wells A4-A6), 25,000 cells/reaction (wells A7-A9), and a no template control ("NTC") (wells A10-A12). Wells B1-B12 (13-24 in FIG. 7) contained reactions without RT, using protease-treated lysates: 250 cells/reaction (wells B1-B3), 2500 cells/reaction (wells B4-B6), 25,000 cells/reaction (wells B7-B9), and a no template control ("NTC") (wells B10-B12). Wells $C_1$-$C_9$ (25-33 in FIG. 7) contained reactions with RT, using protease-untreated lysates: 250 cells/reaction (wells $C_1$-$C_3$), 2500 cells/reaction (wells $C_4$-$C_6$), and 25,000 cells/reaction (wells $C_7$-$C_9$). Wells D1-D9 (37-45 in FIG. 7) contained reactions without RT, using protease-untreated lysates: 250 cells/reaction (wells D1-D3), 2500 cells/reaction (wells D4-D6), and 25,000 cells/reaction (wells D7-D9).

Those data showed that protease treatment of the lysates was necessary in that experiment to detectably amplify either 18S RNA or genomic DNA. Furthermore, the TaqMan One-step qRTPCR reactions worked well to detect 18S RNA or genomic DNA at 250 cells per reaction, but not at 2500 or 25,000 cells per reaction (compare wells 1-3 and 13-15 to wells 4-9 and 15-21 of FIG. 7). Finally, the ΔCt between reactions with RT (wells 1-3) and reactions without RT (wells 13-15) was about 8.5. That ΔCt represents the ΔCt between amplification of 18S RNA and 18S genomic DNA. A diploid Raji cell is estimated to contain about 540 copies of the 18S genomic sequence, and about 1,000,000 copies of 18S RNA. Thus, there is 2,000× more 18S RNA than 18S genomic DNA, which would be predicted to result in a ΔCt of about 11. The difference between the observed ΔCt of 8.5 and the predicted ΔCt of 11 may have resulted from a low efficiency of 18S RNA amplification.

Example 3

Detergent Tests

Different detergents and hydrophilic compounds were tested for their effectiveness in lysing Raji cells and releasing intact nucleic acids, as determined by agarose gel. The following chemicals were tested: NMP (Sigma), Mackernium (CJ Petrow), Empigen (Calbiochem), NDSB-201 (Calbiochem), Zwittergent 3-10 (Calbiochem), Zwittergent 3-14 (Calbiochem), TMACL (Sigma), DDMAB (Calbiochem), CAPSO (Sigma), CHAPS (Calbiochem), LDAO (Calbiochem), Sarkosyl (Sigma), CTAB (Calbiochem), DEDTAB (Fluka), DLS (Sigma), and DTAB (Sigma). Each chemical was tested for lysis at 0.5% in buffer containing 50 mM Tris, pH 8.0, 1 mM EDTA, with 50,000 Raji cells per μl.

Figure 8:
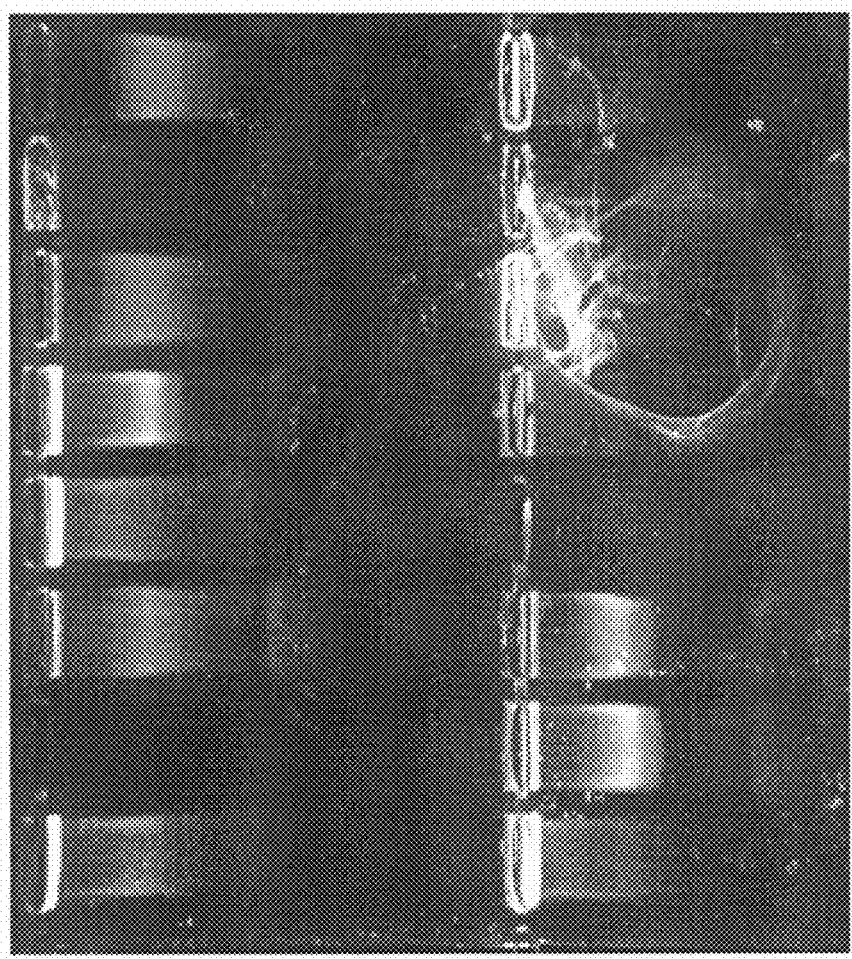
FIG. 8 shows agarose gel electrophoresis of lysates prepared using various chemicals, as described in Example 3. Lanes 1 to 8 are NMP, Mackernium, Empigen, NDSB-201, Zwittergent 3-10, Zwittergent 3-14, TMACL, and DDMAB, respectively. Lanes 9 to 16 are CAPSO, CHAPS, LDAO, Sarkosyl, CTAB, DEDTAB, DLS, and DTAB, respectively.

Exemplary results of agarose gel electrophoresis of the nucleic acids in the lysates are shown in FIG. 8. The top lanes are lysates using NMP, Mackernium, Empigen, NDSB-201, Zwittergent 3-10, Zwittergent 3-14, TMACL, and DDMAB, respectively. The bottom lanes are lysates using CAPSO, CHAPS, LDAO, Sarkosyl, CTAB, DEDTAB, DLS, and DTAB, respectively. From that experiment, NMP, Empigen, NDSB-201, Zwittergent 3-10, Zwittergent 3-14, DDMAB, CAPSO, CHAPS, LDAO, CTAB, DEDTAB, and DTAB were identified as possible candidates for use in the methods described herein.

In addition, screening studies were carried out to determine if the lysates using each chemical contained intact ribosomal RNA bands on agarose gels after heating, and whether the chemicals were compatible with TaqMan One-step qRTPCR reactions at a concentration of 0.1%. (Data not shown.) Following those experiments, NDSB-201 (non-detergent sulfobetaine-201; 3-(1-pyridino)-1-propane sulfonate), LDAO (lauryl dimethylamineoxide), CAPSO (3-(cyclohexylamino)-2-hydroxy-1-propanesulfonic acid), and CHAPS ([3-[(3-cholamidopropyl)-dimethylammonio]-1-propanesulfonate]) were selected for further screening. Experiments looking at inhibition of the proximity ligation assay also suggested that DEDTAB (dodecylethyldimethylammonium bromide) and Zwiftergent 3-10 (n-decyl-N,N-dimethyl-3-ammonio-1-propanesulfonate) are also candidates for use in the described methods. (Data not shown.)

All four chemicals were tested for compatibility in ELISA assays, which would suggest that antigen/antibody interactions are preserved. All four chemicals showed at least partial compatibility in a sandwich ELISA assay using VEGF as the target. (Data not shown.) A second ELISA experiment was carried out using NDSB-201, LDAO, and CAPSO, with PBS as the standard, using 100 μg/ml VEGF, and the R&D Systems VEGF ELISA kit and an ELISA plate reader. In that experiment, CAPSO and LDAO showed comparable background readings, and comparable sample readings to BSA.

NDSB-201 also showed a comparable background reading to BSA, but a higher sample reading than BSA. (Data not shown.)

Figure 9:
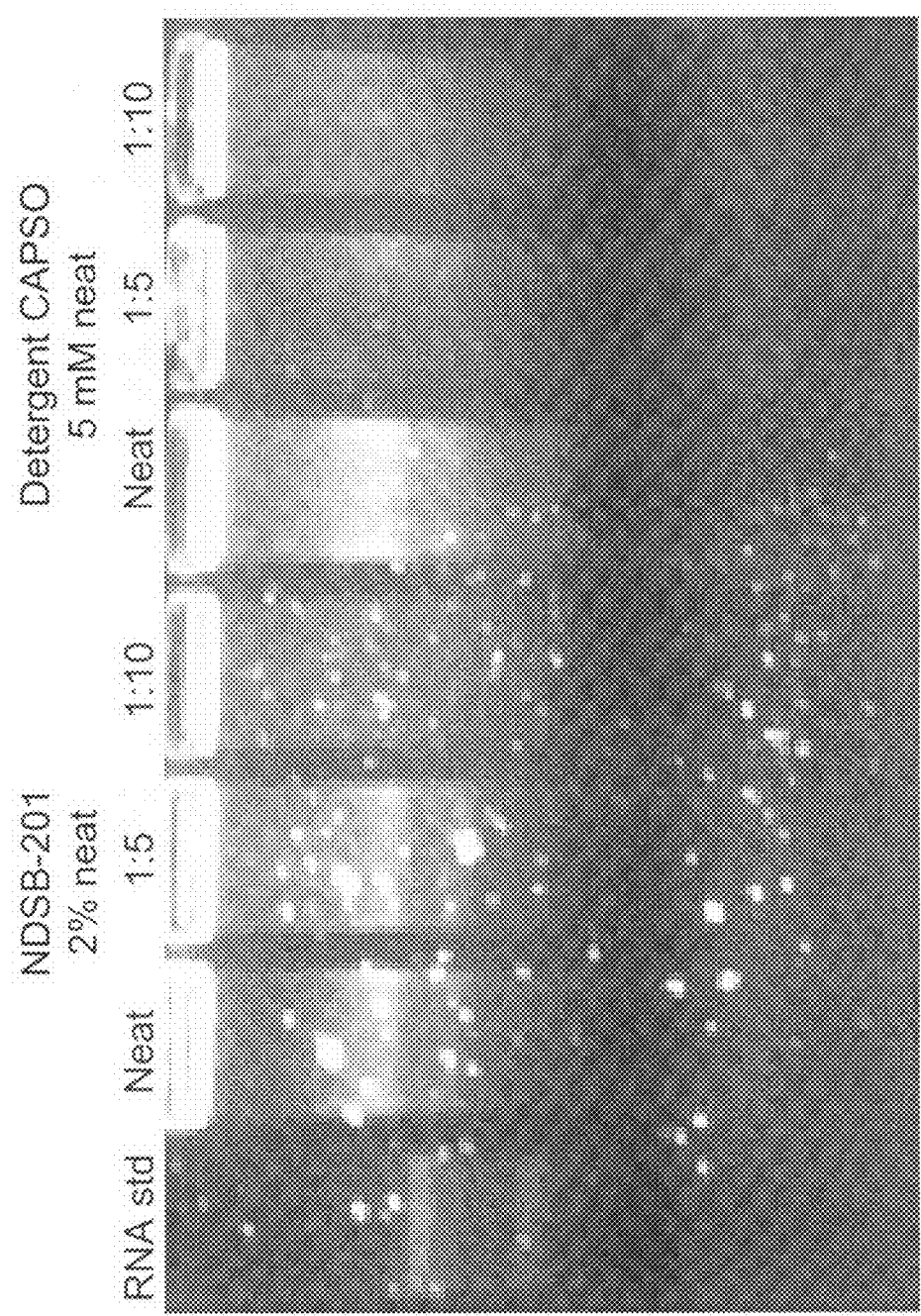
FIG. 9 shows agarose gel electrophoresis of various dilutions of lysates prepared using either 2% NDSB-201 or 5 mM CAPSO, as described in Example 3.

In another experiment, Raji cell lysates were generated in either 2% NDSB-201 or 5 mM CAPSO. Each lysate was then diluted 1:5 and 1:10, and the lysates and lysate dilutions were evaluated for their ability to inhibit RNase degradation of ribosomal RNA during a 30 minute incubation at 37° C., followed by a 5 minute incubation at 50° C. The results are shown in FIG. 9. RNA appears to remain undegraded in all of the samples tested. LDAO was found to be less effective at preserving RNA on prolonged incubation. (Data not shown.)

NDSB-201 is a member of a large family of related chemicals, which includes NDSB-195, -211, -221, -256 and -256-HT. See, e.g., Calbiochem catalog. Each of those chemicals was screened for lysis of Raji cells and preservation of RNA. NDSB-201 performed the best of the chemicals tested in those experiments. (Data not shown.)

Example 4

Additional Reagent Tests

Figure 10:
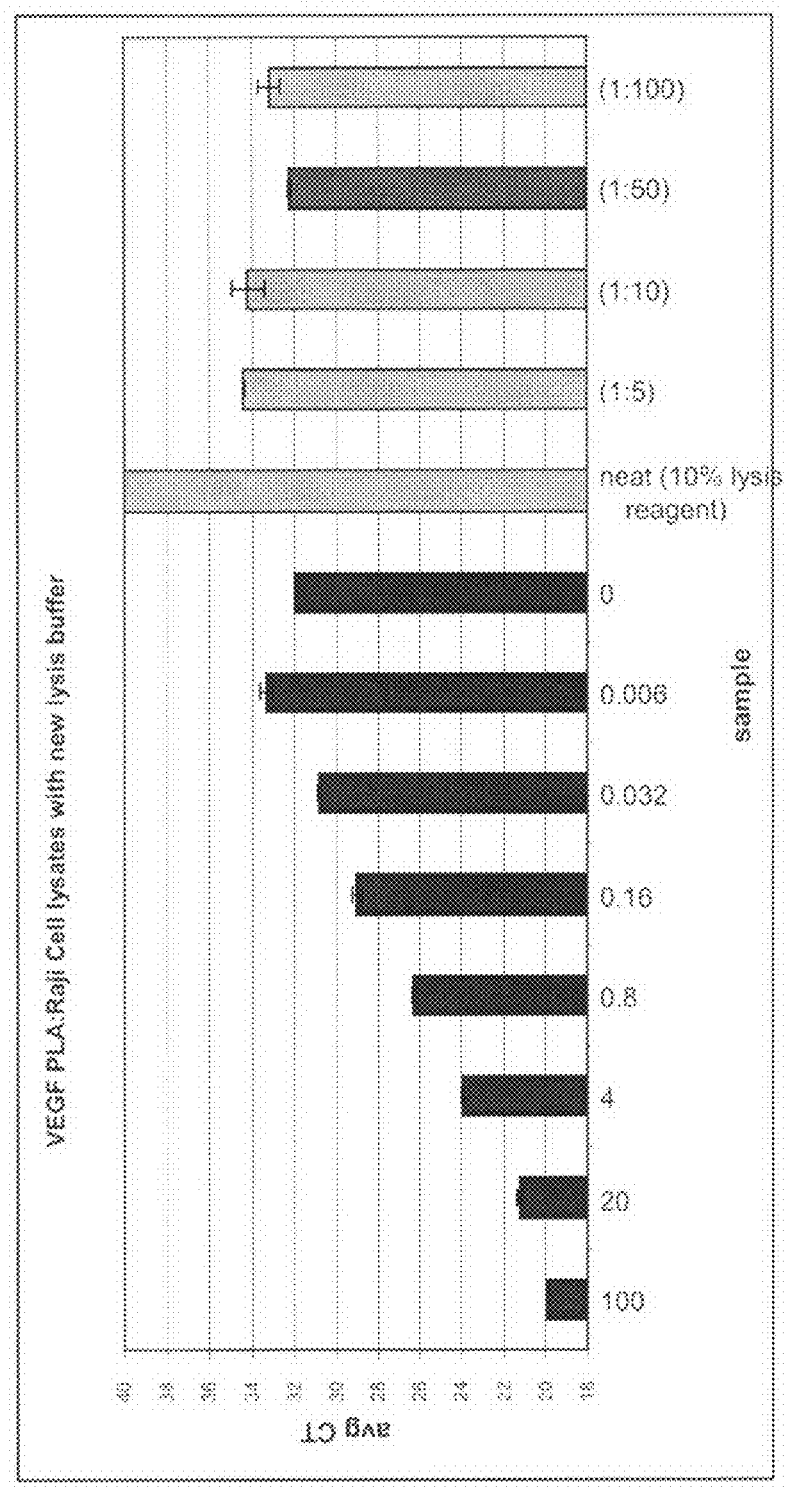
FIG. 10 shows a plot of average threshold cycle number ("avg CT") versus proximity ligation assays using various dilutions of Buffer N lysates, as described in Example 4.

Proximity ligation assays were carried out using various dilutions of Raji cell lysates in Buffer N. Starting with a Raji cell lysate at 50,000 cells per μl in Buffer N, 1:5, 1:10, 1:50, and 1:100 fold dilutions in Buffer D were used in a proximity ligation assay to detect VEGF. The assays were carried out as discussed above in Example 1. The results are shown in FIG. 10. In that experiment, the 1:50 dilution of the lysate, which resulted in 1,000 cells in the 2 μl binding reaction, showed the best results (i.e., the lowest average threshold cycle).

Figure 11:
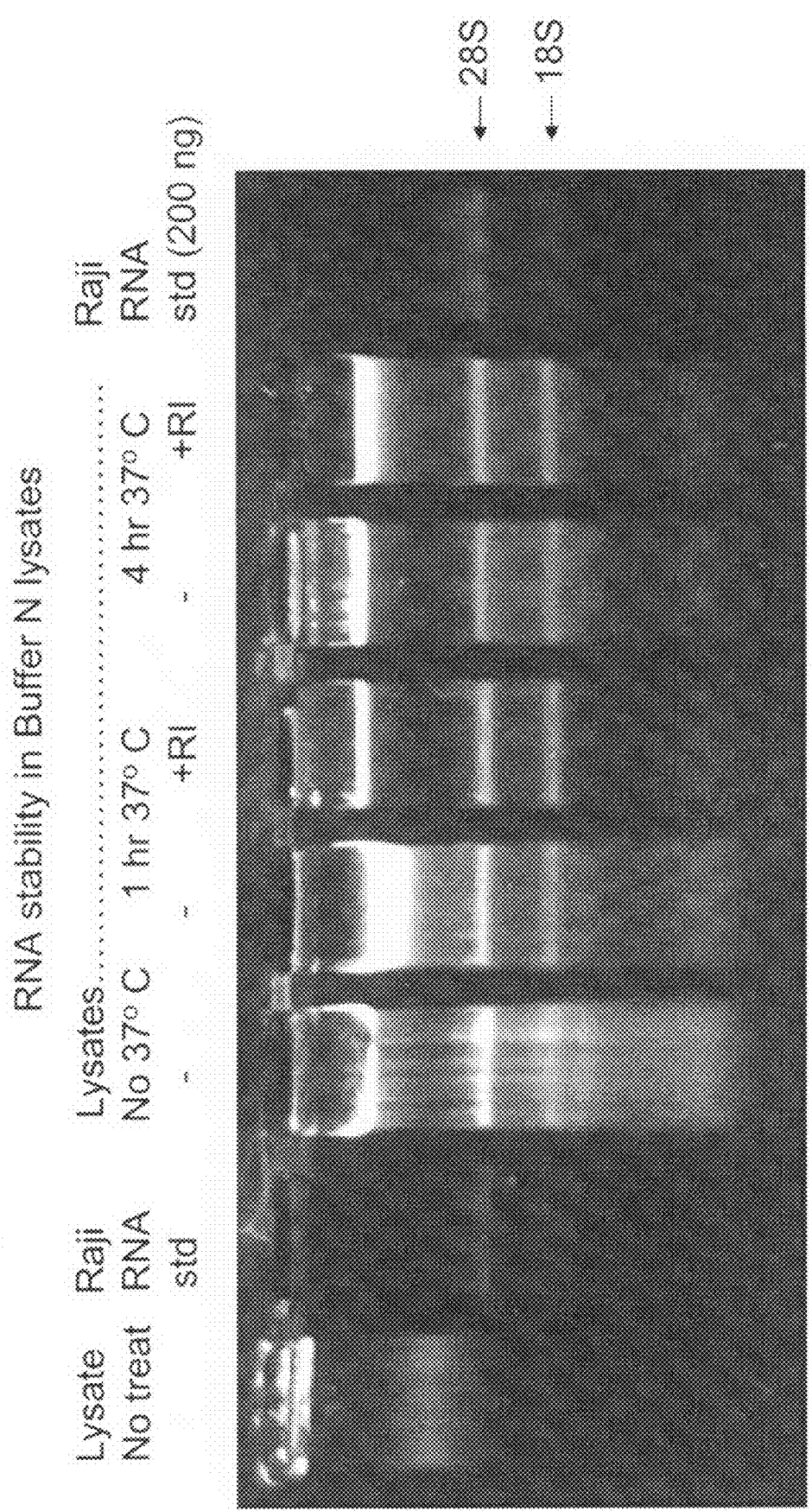
FIG. 11 shows agarose gel electrophoresis of cell lysates incubated for various times at 37° C. with or without RNase inhibitor, as described in Example 4.

An experiment was carried out to determine the stability of RNA in Raji cell lysates in Buffer N. 8 μl lysate (50,000 cells per μl) was incubated with or without 1 μl Anti-RNAse inhibitor (stock is 22 u/μl, Ambion; catalog no. 2690) for 0, 1, or 4 hours at 37° C. After incubation, 32 μl of a solution containing 0.5% SDS and 2 μg/μl proteinase K (Ambion; catalog no. 2546) was added and the lysates were incubated at 55° C. for 30 minutes. 40 μl of 2× glycerol loading buffer (2×GLB; 50% glycerol, 0.5×TBE, containing bromophenol blue and xylene cyanol dyes) was then added to each lysate. 16 μl of the lysates were then loaded on a 1.4% agarose gel. The results are shown in FIG. 11. In that experiment, RNA was stable in the Raji lysates under all conditions tested. Rnase inhibitor was not necessary to preserve the RNA in that experiment.

Figure 12:
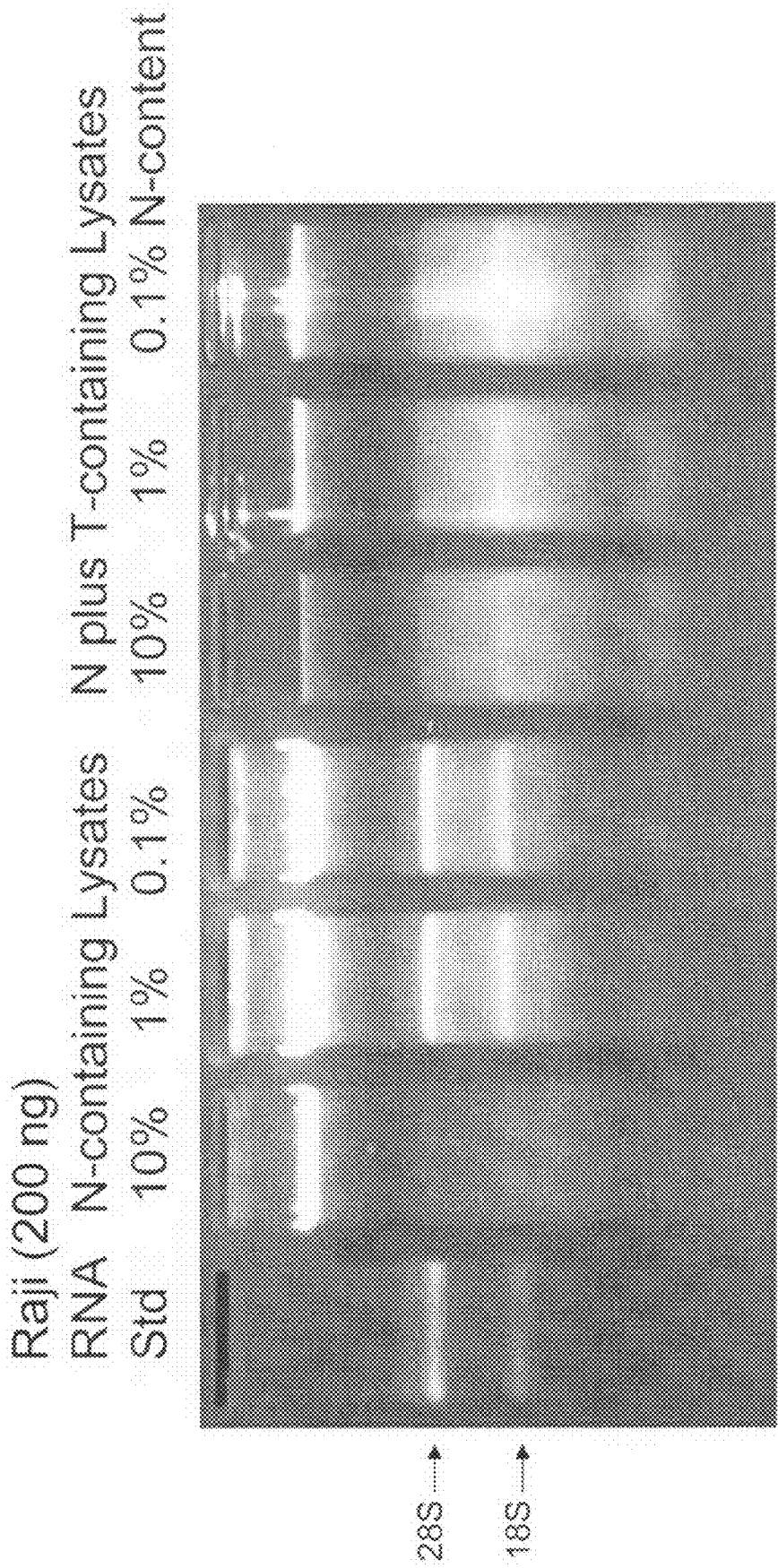
FIG. 12 shows agarose gel electrophoresis of cell lysates in Buffer Na, Buffer Nb, and Buffer Nc, with and without Tween, as described in Example 4.

The effect of Tween-20 was then tested in an RNA stability assay similar to the assay described in the preceding paragraph. In this experiment, Raji cell lysates were made in Buffer Na (10% NDSB-201), Buffer Nb (1% NDSB-201), and Buffer Nc (0.1% NDSB-201), described above, at 50,000 cells per μl. 8 μl lysate was incubated with or without 0.2 μl of 20% Tween-20 (final concentration in lysate, 0.5%) for 4 hours at 37° C. After incubation, 32 μl of a solution containing 0.5% SDS and 2 μg/μl proteinase K was added and the lysates were incubated at 55° C. for 30 minutes. 40 μl of 2×GLB was then added to each lysate. 16 μl of the lysates were then loaded on a 1.4% agarose gel. The results are shown in FIG. 12. RNA was relatively stable in each of the samples containing only NDSB-201, however, RNA was less stable in all samples that also contained Tween-20. Tween-20 therefore appears to be less suitable for use in this experiment.

Figure 13:
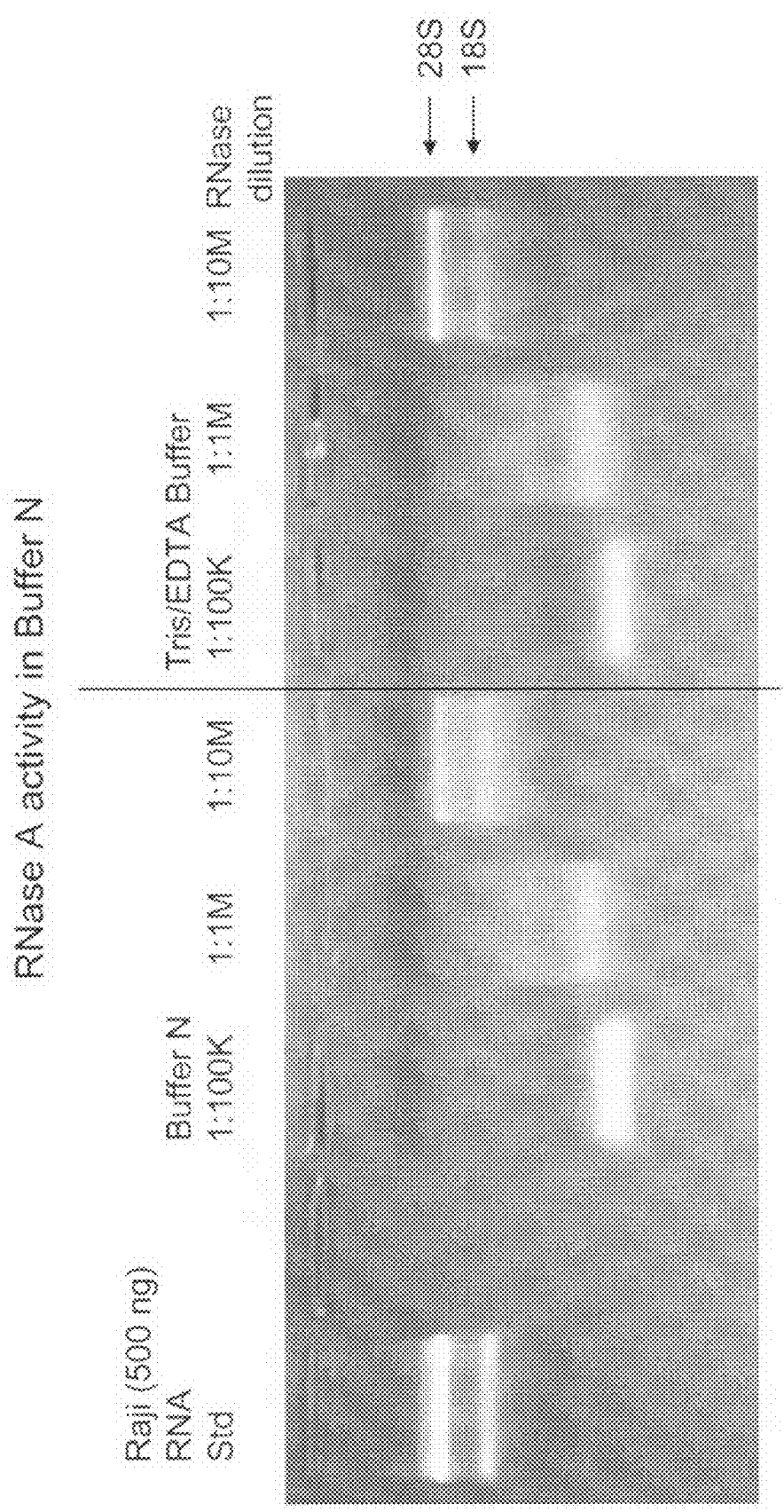
FIG. 13 shows agarose gel electrophoresis of cell lysates in Buffer N, incubated with various concentrations of RNase A, as described in Example 4.

Buffer N was then tested for the ability to inhibit RNase A activity. A 1 mg/ml stock of Rnase A (Ambion; catalog no. 2270) was made in 50 mM Tris pH 8.0, 1 mM EDTA, and 0.5 μg/μl BSA. 10 μl (500 ng) of purified Raji cell RNA (stock is 50 ng/μl; Applied Biosystems TaqMan Control Total RNA (human), catalog no. 4307281) was mixed with 5 μl of 1:100,000, 1:1,000,000, and 1:10,000,000 fold dilutions of the RNase A stock in either Buffer N or 50 mM Tris, 5 mM EDTA pH 8.0. The reactions were incubated for 10 minutes at 37° C. 1 μl of anti-RNase inhibitor (stock is 22 u/μl; Ambion) and 4 μl 5×RNA loading buffer (Ambion; catalog no. 8556; 10× stock used as 5×) was then added and 16 μl of the reactions were loaded on a 1.4% agarose gel. The results are shown in FIG. 13. In that experiment, RNase activity was the same in the reactions containing Buffer N and the reactions containing Tris/EDTA, suggesting that Buffer N does not inhibit RNase A activity. Based on the stability of RNA in lysates made with Buffer N, however, Buffer N may stabilize RNA through mechanisms other than inhibition of RNase A.

Figure 14:
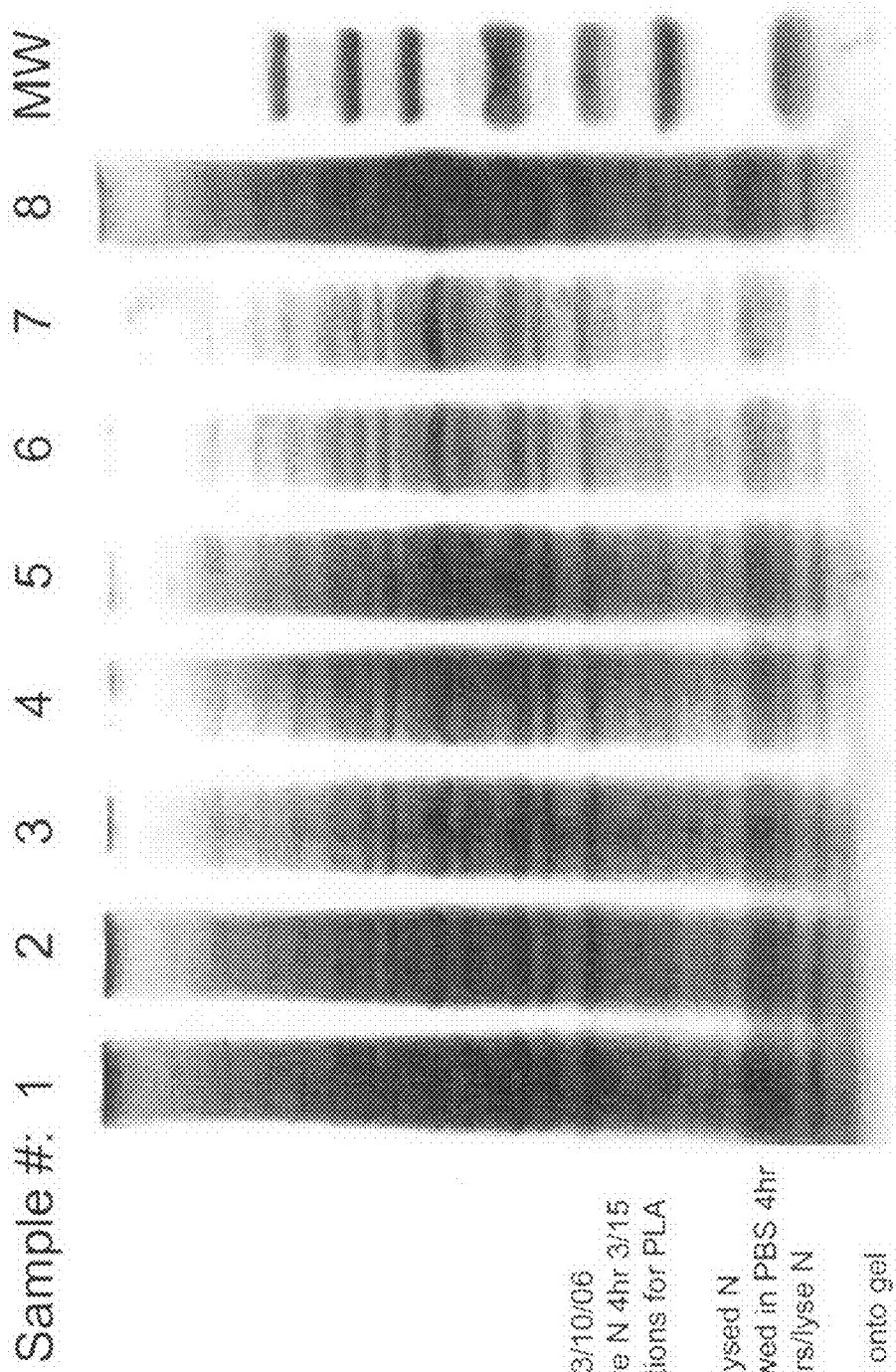
FIG. 14 shows SDS-acrylamide gel electrophoresis of cell lysates in Buffer N under various treatment conditions, as described in Example 4.

FIG. 14 shows protein stability in Raji cell lysates made with Buffer N under various treatment conditions. 10 μl lysate (50,000 cells per μl) made in Buffer N under various conditions were incubated for 4 hours at 37° C. Prior to loading on a 10% SDS-acrylamide gel, the lysates were treated in 1× Novagen SDS-denaturing gel loading buffer (Novagen; catalog no. 70607) at 95° C. for 5 minutes. 1.5 μl of lysate was loaded in each lane. The gel was stained overnight using Pierce Gel Code Stain (Pierce Chemical; catalog no. 24590). In that experiment, Raji cell proteins were stable in Buffer N under numerous conditions, including when incubated for at least 4 hours at 37° C.

Example 5

Protease Tests

Experiments were carried out to determine the suitability of various proteases in the proximity ligation assay and mRNA detection assay discussed in Example 1. Features considered in selecting a protease included whether the protease can be heat-inactivated, whether the protease requires metal ions for activity, whether the protease requires detergents such as SDS, whether the protease digestion degrades RNA, and whether the protease sufficiently liberates RNA.

The following proteases were screened: pepsin (Sigma), collagenase (Sigma), protease type I crude (from bovine pancreas) (Sigma), protease—*subtilisin carlsberg* (Sigma), protease type X—*bacillus thermoproteolyticus* (Calbiochem), protease type XIII—*aspergillus saitoi* (Sigma), protease type XXI—*streptomyces griseus* (Fluka), and proteinase K (Ambion). For each assay, 2 μl of a suspension of Raji cells in PBS (50,000 cells per μl) was mixed with 8 μl of Buffer Na (containing 10% NDSB-201) to lyse the cells. 4 μl of ~20 mg/ml protease was added to the Raji cell lysate, and the mixture was incubated at 37° C. for 30 minutes. After 30 minutes, the viscosity of the lysates was examined. Subtilisin carlsberg protease, *streptomyces griseus* protease, and proteinase K all caused the lysate to become viscous. Bovine pancreas crude protease also cause the lysate to become slightly viscous. The remaining proteases did not significantly increase the viscosity of the lysate.

Figure 15:
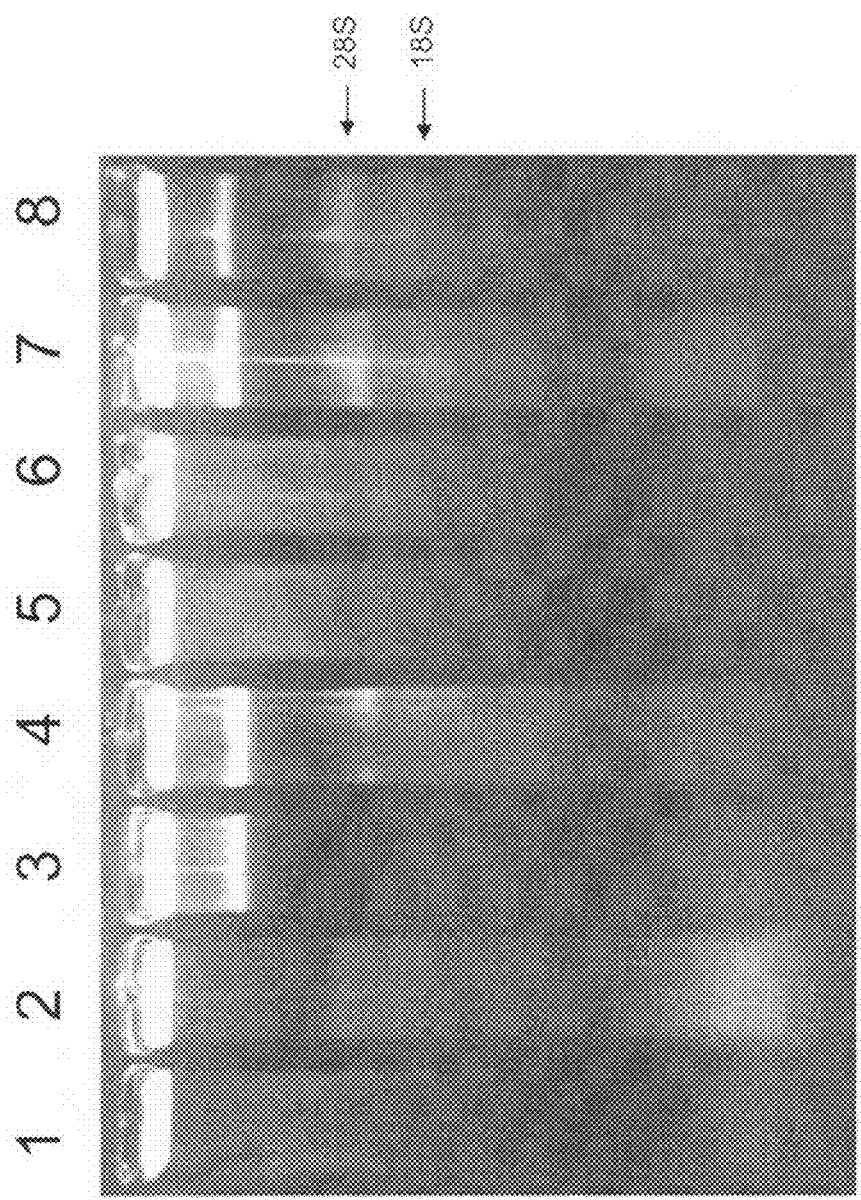
FIG. 15 shows agarose gel electrophoresis of cell lysates in Buffer Na incubated with various proteases, as described in Example 5.

The lysates were then run on a 1.4% agarose gel to determine whether the proteases released RNA and DNA, and whether they caused degradation of RNA and DNA. FIG. 15 shows the results of that experiment. The data shows that subtilisin carlsberg protease, *streptomyces griseus* protease, and proteinase K were most effective at releasing RNA and DNA in the lysates in that experiment. Bovine pancreas crude protease appeared to release DNA, but not RNA, in that experiment. It appears that collagenase may have caused degradation of DNA and/or RNA in that experiment.

A second protease screen was carried out using Raji cells lysed in two different lysis buffers. The first lysis buffer was Buffer Na plus 0.2% LDAO. The second formulation was Buffer Nc. 5 μl of Raji cells in PBS (50,000 cells/μl) was mixed with 5 μl of 2× lysis buffer and incubated at room temperature for 15 minutes. 4 μl of ~20 mg/ml protease was added to the Raji cell lysate, and the mixture was incubated at 37° C. for 30 minutes. 5 μl of 50 mM EDTA was then added, and the lysates were incubated at 75° C. for five minutes. 5 μl of GLB was added and the samples were run on a 1.4% agarose gel. The following proteases were tested in that experiment: pepsin, collagenase, protease—*subtilisin carlsberg*, protease type X—*bacillus thermoproteolyticus*, protease type XIII—*aspergillus saitoi*, protease type XXI—*streptomyces griseus*, and proteinase K.

Figure 16:
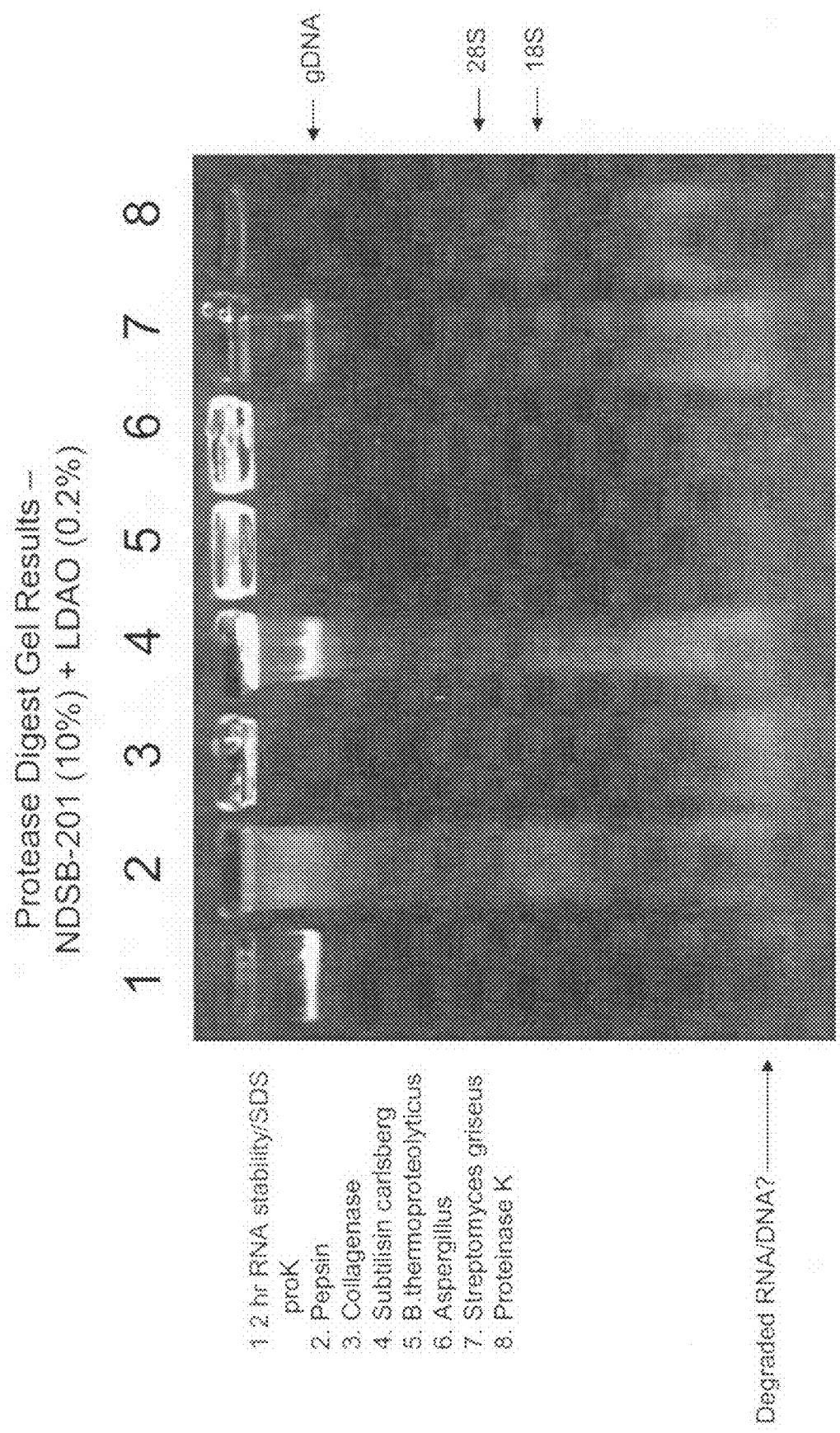
FIG. 16 shows agarose gel electrophoresis of cell lysates in Buffer Na containing 0.2% LDAO incubated with various proteases, as described in Example 5.
Figure 17:
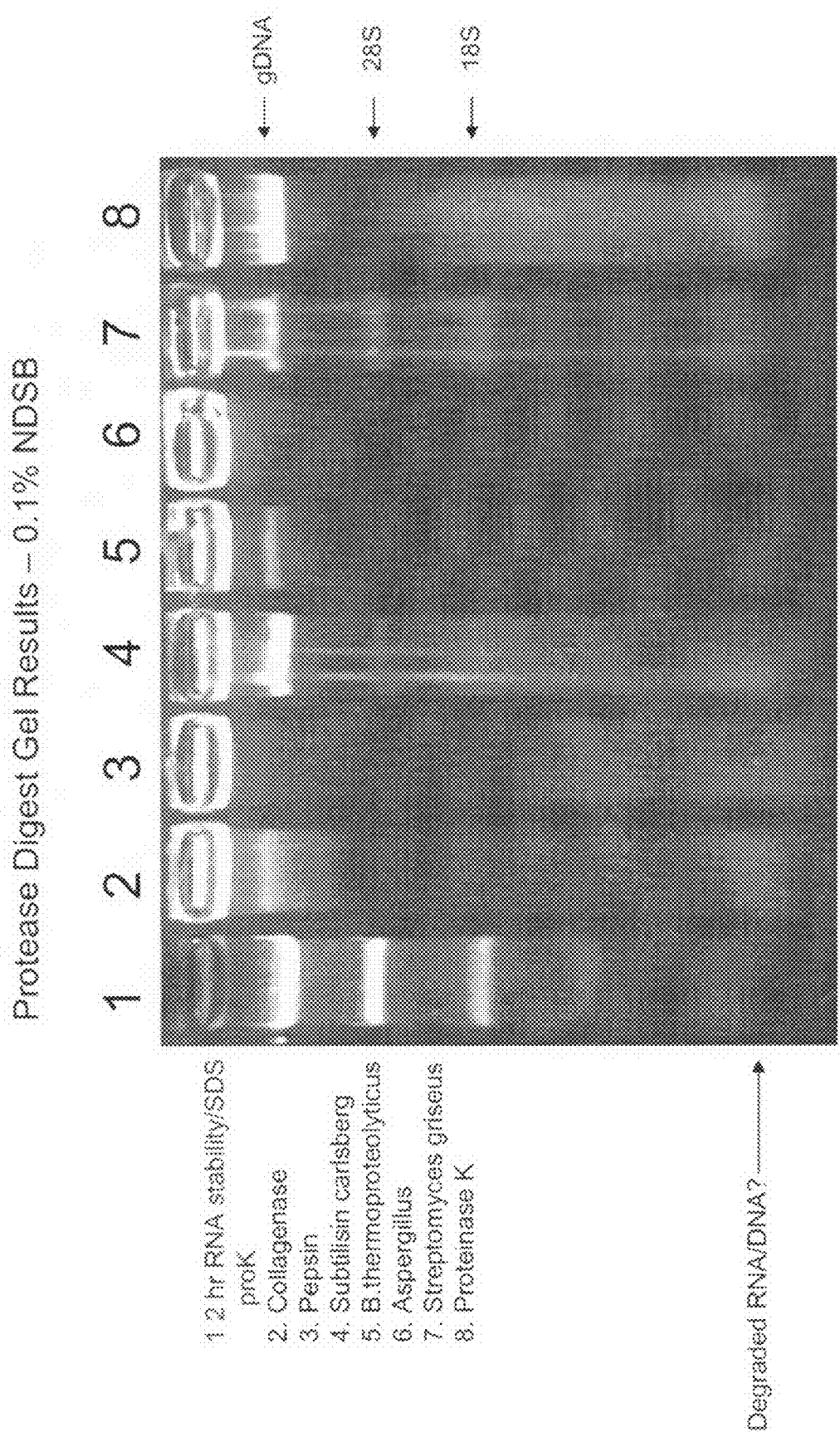
FIG. 17 shows agarose gel electrophoresis of cell lysates in Buffer Nc incubated with various proteases, as described in Example 5.

The results of that experiment are shown in FIGS. 16 and 17. FIG. 16 shows the results using Buffer Na containing 0.2% LDAO, and FIG. 17 shows the results using Buffer Nc. The addition of LDAO to an NDSB-201 containing buffer did not enhance the stability of RNA during protease digestion in that experiment (see FIG. 16).

Although the disclosed teachings have been described with reference to various applications, methods, and compositions, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

We claim:

1. A method of detecting at least one non-nucleic acid target analyte and at least one target nucleic acid in a cell, comprising:
   a) lysing the cell in a multifunctional lysis buffer to produce a cell lysate;
   b) detecting at least one non-nucleic acid target analyte in the cell lysate using a proximity detection assay; and
   c) detecting at least one target nucleic acid in the cell lysate using a quantitative nucleic acid detection assay;
   wherein (b) and (c) occur in the same vessel.

2. The method of claim 1, wherein at least one non-nucleic acid target analyte is selected from a protein, a peptide, a carbohydrate, and a hormone.

3. The method of claim 2, wherein at least one non-nucleic acid target analyte is a protein.

4. The method of claim 1, wherein the proximity detection assay comprises:
   a) incubating the cell lysate with a first proximity detection probe and a second proximity detection probe under conditions allowing interaction between the first and second proximity detection probes; and
   b) detecting the interaction between the first and second proximity detection probes.

5. The method of claim 4, wherein the first proximity detection probe comprises a first oligonucleotide moiety and a first analyte binding moiety, and wherein the second proximity detection probe comprises a second oligonucleotide moiety and a second analyte binding moiety.

6. The method of claim 5, wherein the first analyte binding moiety and the second analyte binding moiety are capable of binding to the same target analyte.

7. The method of claim 5, wherein the first analyte binding moiety and the second analyte binding moiety are capable of binding to different target analytes.

8. The method of claim 5, wherein the interaction between the first and second proximity detection probes comprises at least one method selected from hybridization between the first and second oligonucleotide moieties and ligation of the first and second oligonucleotide moieties.

9. The method of claim 8, wherein the interaction between the first and second proximity detection probes comprises ligation of the first and second oligonucleotide moieties.

10. The method of claim 4, wherein the incubating comprises at least one splint oligonucleotide.

11. The method of claim 1, wherein the at least one target nucleic acid is at least one mRNA.

12. The method of claim 11, wherein the quantitative nucleic acid detection assay comprises reverse-transcription and real-time PCR.

13. The method of claim 1, wherein at least one of the at least one target nucleic acids encodes at least one of the at least one non-nucleic acid target analytes.

14. The method of claim 1, wherein the multifunctional lysis buffer comprises at least one chemical selected from NDSB-201, LDAO, CHAPS, DEDTAB, Zwittergent 3-10, and CAPSO.

15. The method of claim 14, wherein the multifunctional lysis buffer comprises NDSB-201.

16. The method of claim 1, wherein the detecting the at least one non-nucleic acid target analyte comprises a first real-time PCR reaction and the detecting the at least one target nucleic acid comprises a second real-time PCR reaction.

17. A kit for detecting at least one target analyte and at least one target nucleic acid, comprising:
   at least one multifunctional lysis buffer comprising at least one chemical selected from NDSB-201, CHAPS, DEDTAB, Zwittergent 3-10, and CAPSO; and
   at least one ligase.

* * * * *